US008357811B2

(12) United States Patent
Liao et al.

(10) Patent No.: US 8,357,811 B2
(45) Date of Patent: Jan. 22, 2013

(54) CRYSTALLINE FORMS OF DOCETAXEL AND PROCESS FOR PREPARATION THEREOF

(75) Inventors: Yuan-Xiu Liao, Kaohsiung (TW); Meng-Fen Ho, Anding Township, Tainan County (TW); Shu-Ping Chen, Kaohsiung (TW); Chia-Ning Lin, Pingtung (TW); Yu-Li Lin, Yongkang (TW); Tsung-Yu Hsiao, Neimen Township, Kaohsiung County (TW)

(73) Assignee: ScnioPharm Singapore PTE Ltd., Singapore (SG)

( * ) Notice: Subject to any disclaimer, the term of this patent is extended or adjusted under 35 U.S.C. 154(b) by 770 days.

(21) Appl. No.: 12/501,883

(22) Filed: Jul. 13, 2009

(65) Prior Publication Data
US 2009/0275762 A1 Nov. 5, 2009

Related U.S. Application Data

(62) Division of application No. 11/975,511, filed on Oct. 19, 2007, now Pat. No. 7,662,980.

(60) Provisional application No. 60/853,341, filed on Oct. 20, 2006.

(51) Int. Cl.
C07D 305/14 (2006.01)
(52) U.S. Cl. .................... 549/510; 549/511
(58) Field of Classification Search .......... 549/510, 549/511
See application file for complete search history.

(56) References Cited

U.S. PATENT DOCUMENTS

| 4,814,470 | A | 3/1989 | Colin et al. |
|---|---|---|---|
| 4,924,012 | A | 5/1990 | Colin et al. |
| 5,229,526 | A | 7/1993 | Holton |
| 5,476,954 | A | 12/1995 | Bourzat et al. |
| 5,621,121 | A | 4/1997 | Commercon et al. |
| 5,637,723 | A | 6/1997 | Commercon et al. |
| 5,688,977 | A | 11/1997 | Sisti et al. |
| 5,723,635 | A | 3/1998 | Durand et al. |
| 5,726,318 | A | 3/1998 | Commercon et al. |
| 5,861,515 | A | 1/1999 | Commercon et al. |
| 5,917,062 | A | 6/1999 | Bombardelli |
| 6,008,385 | A | 12/1999 | Durand et al. |
| 6,022,985 | A | 2/2000 | Authelin et al. |
| 6,197,980 | B1 | 3/2001 | Durand et al. |
| 6,531,611 | B2 | 3/2003 | Schloemer et al. |
| 6,838,569 | B2 | 1/2005 | Sharma et al. |
| 2003/0225291 | A1 | 12/2003 | Sharma et al. |
| 2004/0116720 | A1 | 6/2004 | Sharma et al. |
| 2006/0217436 | A1 | 9/2006 | Li et al. |
| 2007/0142457 | A1 | 6/2007 | Pontiroli et al. |

FOREIGN PATENT DOCUMENTS

| WO | WO 93/06094 | 4/1993 |
|---|---|---|
| WO | WO 2005/061747 | 7/2005 |
| WO | WO 2007/044950 | 4/2007 |
| WO | WO2007/109654 | 9/2007 |

OTHER PUBLICATIONS

Zaske, et al., Docetaxel (Taxotere® Trihydrate) Forms: Crystal Structure Determination from XRPD & XRSCD Data, vols. 443-444 (2004) pp. 411-414.

(Continued)

*Primary Examiner* — Andrew D Kosar
*Assistant Examiner* — Raymond Covington
(74) *Attorney, Agent, or Firm* — Enshan Hong; VLP Law Group LLP

(57) ABSTRACT

New anhydrous crystalline form of docetaxel and process of making anhydrous docetaxel and docetaxel trihydrate are provided.

6 Claims, 31 Drawing Sheets

OTHER PUBLICATIONS

Extended European Search Report for EP07861453 application dated Dec. 3, 2010.
Gueritte-Voegelein, F., et al., Structure of a synthetic taxol precursor: N-tert-butoxycarony1-10-deacetyl-N-debenzoyltaol. 7S-Crystallogr., Liquid Crystals vol. 113, 1990.
Harvey, S.D. et al., Separation of taxol from related taxanes in *Taxus brevifolia* extracts by isocratic elution reversed-phase microcolumn high-performance liquid chromatography, Journal of Chromatography, 587 (1991) 300-305.
Written Opinion of the International Search Authority issued Mar. 14, 2009 in re International application No. PCT/US07/22309.
International Search Report Issued by the International Search Authority on Mar. 14, 2009 in re International application No. PCT/US07/22309.
Amendment Under Article 34 filed Jul. 9, 2008 in response to Written Opinion dated Mar. 14, 2008 for PCT/US07/22309.

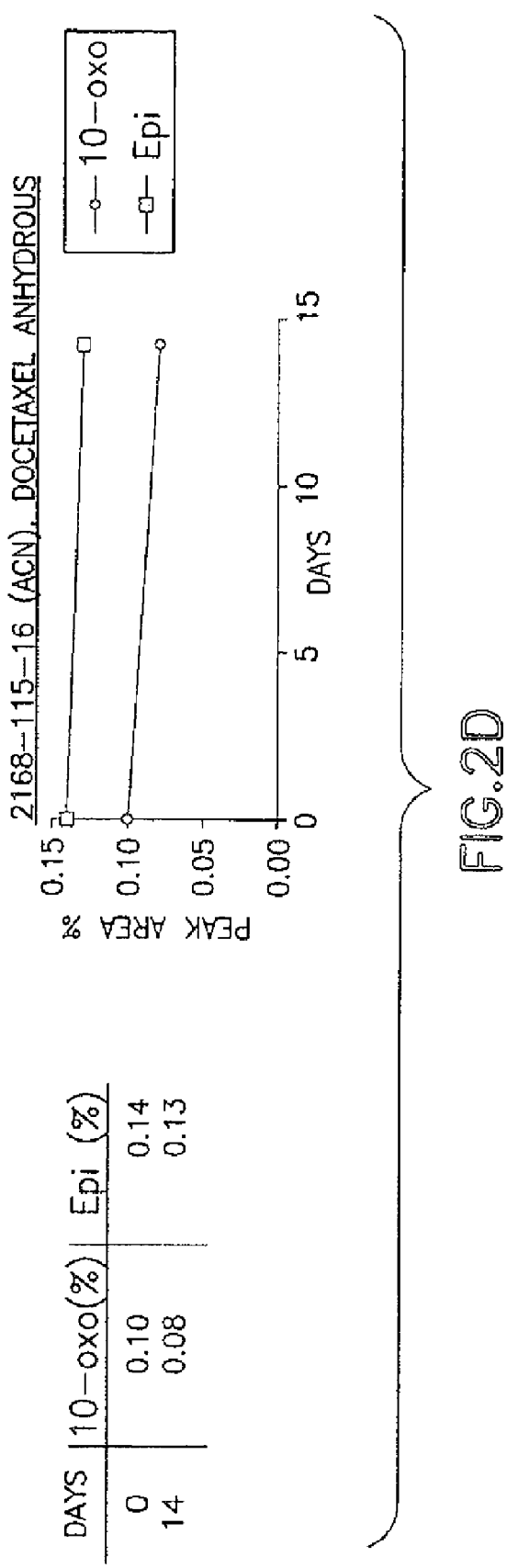

FILE: UNTITLED1

ID: SPT1141API

COMMENT:

SCAN TYPE: NORMAL

START ANGLE: 2 DEG.

STOP ANGLE: 40 DEG.

NUM POINTS: 1901

STEP SIZE: 0.02 DEG.

DATAFILE RES: 1600

SCAN RATE: 2.000000

SCAN MODE: CONTINUOUS

WAVELENGTH: 1.54056

DIFFRACTOMETER OPTICS:
  DETECTOR:
    TYPE: FIXED SLITS
    X2 CONFIGURATION: NO
  TUBE:
    TYPE: FIXED SLITS
    X2 CONFIGURATION: NO

FIG.4A

| PEAKS: | | | | | | |
|---|---|---|---|---|---|---|
| POSITION | | ESD | CORR. FACT | INTENSITY | REL. INT. | FWHM (L) |
| (Deg.) | (DSp.) | (Deg.) | | (CPS) | (%) | |
| 4.6319 | 19.0618 | 0.0000 | 0.0000 | 1007.97 | 16.47 | 0.1600 |
| 7.9988 | 11.0442 | 0.0000 | 0.0000 | 6120.42 | 100.00 | 0.1600 |
| 9.1763 | 9.6294 | 0.0000 | 0.0000 | 1221.58 | 19.96 | 0.1600 |
| 11.2681 | 7.8460 | 0.0000 | 0.0000 | 2096.80 | 34.26 | 0.1600 |
| 12.4388 | 7.1101 | 0.0000 | 0.0000 | 3297.00 | 53.87 | 0.1600 |
| 13.1044 | 6.7504 | 0.0000 | 0.0000 | 536.93 | 8.77 | 0.0800 |
| 13.8138 | 6.4053 | 0.0000 | 0.0000 | 1560.50 | 25.50 | 0.1600 |
| 15.3800 | 5.7564 | 0.0000 | 0.0000 | 1756.73 | 28.70 | 0.1600 |
| 16.8244 | 5.2653 | 0.0000 | 0.0000 | 3510.17 | 57.35 | 0.1600 |
| 18.1375 | 4.8870 | 0.0000 | 0.0000 | 830.97 | 13.58 | 0.1600 |
| 18.3600 | 4.8282 | 0.0000 | 0.0000 | 648.53 | 10.60 | 0.1600 |
| 19.4800 | 4.5531 | 0.0000 | 0.0000 | 920.00 | 15.03 | 0.1200 |
| 20.3006 | 4.3709 | 0.0000 | 0.0000 | 1734.52 | 28.34 | 0.1600 |
| 20.8137 | 4.2642 | 0.0000 | 0.0000 | 820.57 | 13.41 | 0.1600 |
| 22.4000 | 3.9657 | 0.0000 | 0.0000 | 557.53 | 9.11 | 0.1600 |
| 22.5138 | 3.9459 | 0.0000 | 0.0000 | 609.77 | 9.96 | 0.1600 |
| 22.7400 | 3.9072 | 0.0000 | 0.0000 | 516.67 | 8.44 | 0.1600 |
| 23.3481 | 3.8068 | 0.0000 | 0.0000 | 1733.32 | 28.32 | 0.1600 |
| 23.7044 | 3.7504 | 0.0000 | 0.0000 | 960.75 | 15.70 | 0.1600 |
| 24.1187 | 3.6869 | 0.0000 | 0.0000 | 658.47 | 10.76 | 0.1600 |
| 25.1138 | 3.5430 | 0.0000 | 0.0000 | 361.68 | 5.91 | 0.1600 |
| 25.2200 | 3.5283 | 0.0000 | 0.0000 | 503.33 | 8.22 | 0.1400 |
| 26.7200 | 3.3336 | 0.0000 | 0.0000 | 453.33 | 7.41 | 0.1600 |
| 26.7725 | 3.3271 | 0.0000 | 0.0000 | 432.43 | 7.07 | 0.1600 |
| 28.3444 | 3.1461 | 0.0000 | 0.0000 | 634.00 | 10.36 | 0.1600 |
| 29.2325 | 3.0525 | 0.0000 | 0.0000 | 538.18 | 8.79 | 0.1600 |
| 30.6200 | 2.9173 | 0.0000 | 0.0000 | 640.17 | 10.46 | 0.1600 |
| 31.9831 | 2.7960 | 0.0000 | 0.0000 | 498.47 | 8.14 | 0.1600 |
| 34.0412 | 2.6315 | 0.0000 | 0.0000 | 355.78 | 5.81 | 0.1400 |
| 35.2350 | 2.5450 | 0.0000 | 0.0000 | 420.27 | 6.87 | 0.1600 |
| 35.4331 | 2.5313 | 0.0000 | 0.0000 | 427.08 | 6.98 | 0.1600 |
| 35.5788 | 2.5212 | 0.0000 | 0.0000 | 453.28 | 7.41 | 0.1600 |

FIG. 4B

| FSD (Deg.) | AREA | SOURCE | CURVE | STRAIN | CSize | CSize SOURCE |
|---|---|---|---|---|---|---|
| 0.0000 | 161.3 | PFind | NONE | 0.00 | 0.00 | NONE |
| 0.0000 | 979.3 | PFind | NONE | 0.00 | 0.00 | NONE |
| 0.0000 | 195.5 | PFind | NONE | 0.00 | 0.00 | NONE |
| 0.0000 | 335.5 | PFind | NONE | 0.00 | 0.00 | NONE |
| 0.0000 | 527.5 | PFind | NONE | 0.00 | 0.00 | NONE |
| 0.0000 | 85.9 | PFind | NONE | 0.00 | 0.00 | NONE |
| 0.0000 | 249.7 | PFind | NONE | 0.00 | 0.00 | NONE |
| 0.0000 | 281.1 | PFind | NONE | 0.00 | 0.00 | NONE |
| 0.0000 | 561.6 | PFind | NONE | 0.00 | 0.00 | NONE |
| 0.0000 | 133.0 | PFind | NONE | 0.00 | 0.00 | NONE |
| 0.0000 | 103.8 | PFind | NONE | 0.00 | 0.00 | NONE |
| 0.0000 | 110.4 | PFind | NONE | 0.00 | 0.00 | NONE |
| 0.0000 | 277.5 | PFind | NONE | 0.00 | 0.00 | NONE |
| 0.0000 | 131.3 | PFind | NONE | 0.00 | 0.00 | NONE |
| 0.0000 | 89.2 | PFind | NONE | 0.00 | 0.00 | NONE |
| 0.0000 | 97.6 | PFind | NONE | 0.00 | 0.00 | NONE |
| 0.0000 | 82.7 | PFind | NONE | 0.00 | 0.00 | NONE |
| 0.0000 | 277.3 | PFind | NONE | 0.00 | 0.00 | NONE |
| 0.0000 | 153.7 | PFind | NONE | 0.00 | 0.00 | NONE |
| 0.0000 | 105.4 | PFind | NONE | 0.00 | 0.00 | NONE |
| 0.0000 | 57.9 | PFind | NONE | 0.00 | 0.00 | NONE |
| 0.0000 | 40.3 | PFind | NONE | 0.00 | 0.00 | NONE |
| 0.0000 | 72.5 | PFind | NONE | 0.00 | 0.00 | NONE |
| 0.0000 | 60.5 | PFind | NONE | 0.00 | 0.00 | NONE |
| 0.0000 | 101.4 | PFind | NONE | 0.00 | 0.00 | NONE |
| 0.0000 | 86.1 | PFind | NONE | 0.00 | 0.00 | NONE |
| 0.0000 | 102.4 | PFind | NONE | 0.00 | 0.00 | NONE |
| 0.0000 | 79.8 | PFind | NONE | 0.00 | 0.00 | NONE |
| 0.0000 | 56.9 | PFind | NONE | 0.00 | 0.00 | NONE |
| 0.0000 | 67.2 | PFind | NONE | 0.00 | 0.00 | NONE |
| 0.0000 | 68.3 | PFind | NONE | 0.00 | 0.00 | NONE |
| 0.0000 | 63.5 | PFind | NONE | 0.00 | 0.00 | NONE |

FIG.4C

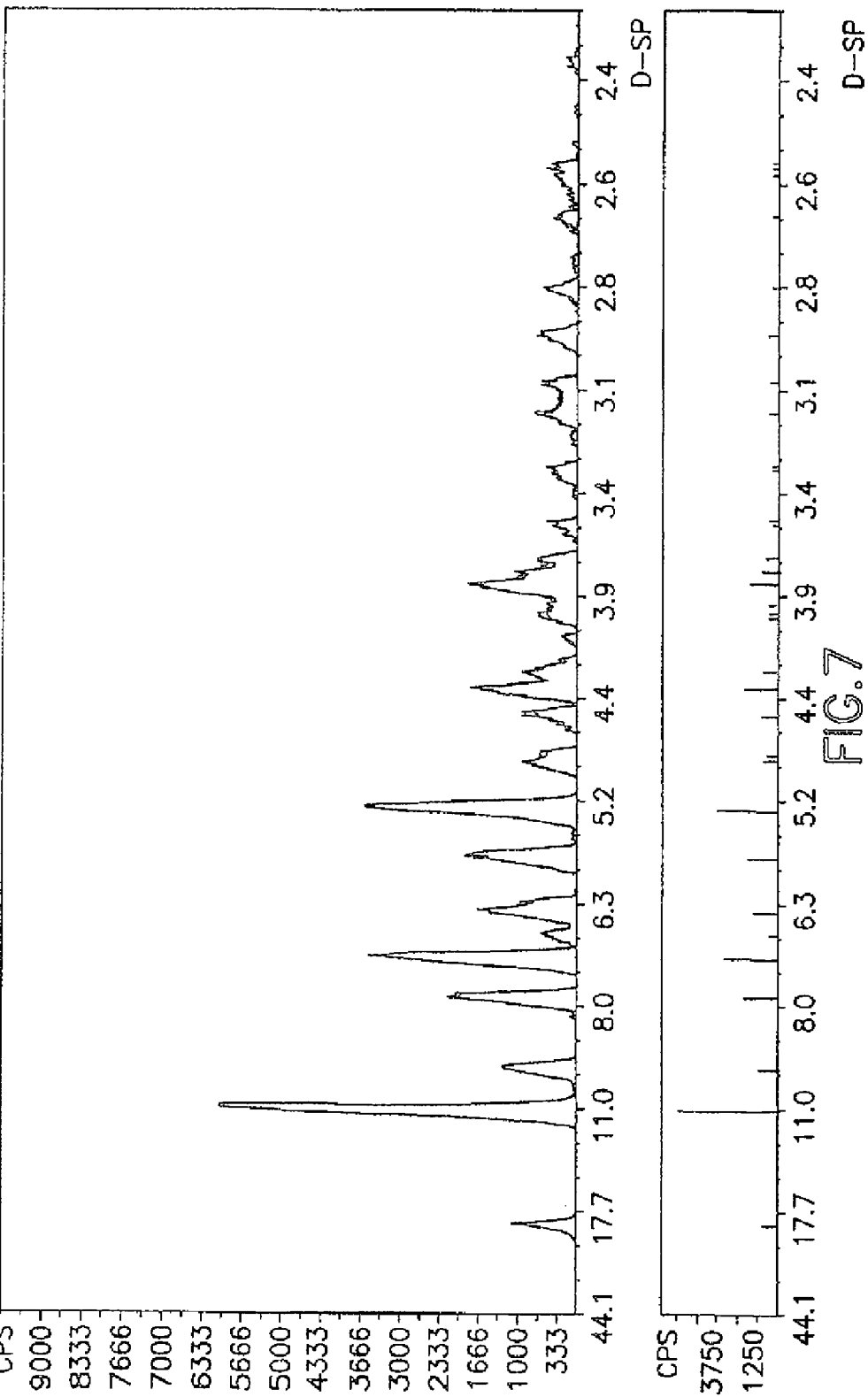

FILE: UNTITLED2

ID: SPT1141API
COMMENT: B#70745AR002
SCAN TYPE: NORMAL
START ANGLE: 2 DEG.
STOP ANGLE: 40 DEG.
NUM POINTS: 1901
STEP SIZE: 0.02 DEG.
DATAFILE RES: 1600
SCAN RATE: 2.000000
SCAN MODE: CONTINUOUS
WAVELENGTH: 1.540562

DIFFRACTOMETER OPTICS:
   DETECTOR:
      TYPE: FIXED SLITS
      X2 CONFIGURATION: NO

TUBE:
      TYPE: FIXED SLITS
      X2 CONFIGURATION: NO

FIG.8A

PEAKS:

| POSITION (Deg.) | (DSp.) | ESD (Deg.) | CORR. FACT | INTENSITY (CPS) | REL. INT. (%) | FWHM (L) |
|---|---|---|---|---|---|---|
| 4.6319 | 19.0618 | 0.0000 | 0.0000 | 1007.97 | 16.47 | 0.1600 |
| 7.9988 | 11.0442 | 0.0000 | 0.0000 | 6120.42 | 100.00 | 0.1600 |
| 9.1763 | 9.6294 | 0.0000 | 0.0000 | 1221.58 | 19.96 | 0.1600 |
| 11.2681 | 7.8460 | 0.0000 | 0.0000 | 2096.80 | 34.26 | 0.1600 |
| 12.4388 | 7.1101 | 0.0000 | 0.0000 | 3297.00 | 53.87 | 0.1600 |
| 13.1044 | 6.7504 | 0.0000 | 0.0000 | 536.93 | 8.77 | 0.0800 |
| 13.8138 | 6.4053 | 0.0000 | 0.0000 | 1560.50 | 25.50 | 0.1600 |
| 15.3800 | 5.7564 | 0.0000 | 0.0000 | 1756.73 | 28.70 | 0.1600 |
| 16.8244 | 5.2653 | 0.0000 | 0.0000 | 3510.17 | 57.35 | 0.1600 |
| 18.1375 | 4.8870 | 0.0000 | 0.0000 | 830.97 | 13.58 | 0.1600 |
| 18.3600 | 4.8282 | 0.0000 | 0.0000 | 648.53 | 10.60 | 0.1600 |
| 19.4860 | 4.5531 | 0.0000 | 0.0000 | 920.00 | 15.03 | 0.1200 |
| 20.3006 | 4.3709 | 0.0000 | 0.0000 | 1734.52 | 28.34 | 0.1600 |
| 20.8137 | 4.2642 | 0.0000 | 0.0000 | 820.57 | 13.41 | 0.1600 |
| 22.4000 | 3.9657 | 0.0000 | 0.0000 | 557.53 | 9.11 | 0.1600 |
| 22.5138 | 3.9459 | 0.0000 | 0.0000 | 609.77 | 9.96 | 0.1600 |
| 22.7400 | 3.9072 | 0.0000 | 0.0000 | 516.67 | 8.44 | 0.1600 |
| 23.3481 | 3.8068 | 0.0000 | 0.0000 | 1733.32 | 28.32 | 0.1600 |
| 23.7044 | 3.7504 | 0.0000 | 0.0000 | 960.75 | 15.70 | 0.1600 |
| 24.1187 | 3.6869 | 0.0000 | 0.0000 | 658.47 | 10.76 | 0.1600 |
| 25.1138 | 3.5430 | 0.0000 | 0.0000 | 361.68 | 5.91 | 0.1600 |
| 25.2200 | 3.5283 | 0.0000 | 0.0000 | 503.33 | 8.22 | 0.1400 |
| 26.7200 | 3.3336 | 0.0000 | 0.0000 | 453.33 | 7.41 | 0.1600 |
| 26.7725 | 3.3271 | 0.0000 | 0.0000 | 432.43 | 7.07 | 0.1600 |
| 28.3444 | 3.1461 | 0.0000 | 0.0000 | 634.00 | 10.36 | 0.1600 |
| 29.2325 | 3.0525 | 0.0000 | 0.0000 | 538.18 | 8.79 | 0.1600 |
| 30.6200 | 2.9173 | 0.0000 | 0.0000 | 640.17 | 10.46 | 0.1600 |
| 31.9831 | 2.7960 | 0.0000 | 0.0000 | 498.47 | 8.14 | 0.1600 |
| 34.0412 | 2.6315 | 0.0000 | 0.0000 | 355.78 | 5.81 | 0.1400 |
| 35.2350 | 2.5450 | 0.0000 | 0.0000 | 420.27 | 6.87 | 0.1600 |
| 35.4331 | 2.5313 | 0.0000 | 0.0000 | 427.08 | 6.98 | 0.1600 |
| 35.5700 | 2.5212 | 0.0000 | 0.0000 | 453.28 | 7.41 | 0.1600 |

FIG. 8B

| ESD (Deg.) | AREA | SOURCE | CURVE | STRAIN | CSize | CSize SOURCE |
|---|---|---|---|---|---|---|
| 0.0000 | 161.3 | PFind | NONE | 0.00 | 0.00 | NONE |
| 0.0000 | 979.3 | PFind | NONE | 0.00 | 0.00 | NONE |
| 0.0000 | 195.5 | PFind | NONE | 0.00 | 0.00 | NONE |
| 0.0000 | 335.5 | PFind | NONE | 0.00 | 0.00 | NONE |
| 0.0000 | 527.5 | PFind | NONE | 0.00 | 0.00 | NONE |
| 0.0000 | 85.0 | PFind | NONE | 0.00 | 0.00 | NONE |
| 0.0000 | 249.7 | PFind | NONE | 0.00 | 0.00 | NONE |
| 0.0000 | 281.1 | PFind | NONE | 0.00 | 0.00 | NONE |
| 0.0000 | 561.6 | PFind | NONE | 0.00 | 0.00 | NONE |
| 0.0000 | 133.0 | PFind | NONE | 0.00 | 0.00 | NONE |
| 0.0000 | 103.8 | PFind | NONE | 0.00 | 0.00 | NONE |
| 0.0000 | 110.4 | PFind | NONE | 0.00 | 0.00 | NONE |
| 0.0000 | 277.5 | PFind | NONE | 0.00 | 0.00 | NONE |
| 0.0000 | 131.3 | PFind | NONE | 0.00 | 0.00 | NONE |
| 0.0000 | 89.2 | PFind | NONE | 0.00 | 0.00 | NONE |
| 0.0000 | 97.6 | PFind | NONE | 0.00 | 0.00 | NONE |
| 0.0000 | 82.7 | PFind | NONE | 0.00 | 0.00 | NONE |
| 0.0000 | 277.3 | PFind | NONE | 0.00 | 0.00 | NONE |
| 0.0000 | 153.7 | PFind | NONE | 0.00 | 0.00 | NONE |
| 0.0000 | 105.4 | PFind | NONE | 0.00 | 0.00 | NONE |
| 0.0000 | 57.9 | PFind | NONE | 0.00 | 0.00 | NONE |
| 0.0000 | 40.3 | PFind | NONE | 0.00 | 0.00 | NONE |
| 0.0000 | 72.5 | PFind | NONE | 0.00 | 0.00 | NONE |
| 0.0000 | 60.5 | PFind | NONE | 0.00 | 0.00 | NONE |
| 0.0000 | 101.4 | PFind | NONE | 0.00 | 0.00 | NONE |
| 0.0000 | 86.1 | PFind | NONE | 0.00 | 0.00 | NONE |
| 0.0000 | 102.4 | PFind | NONE | 0.00 | 0.00 | NONE |
| 0.0000 | 79.8 | PFind | NONE | 0.00 | 0.00 | NONE |
| 0.0000 | 56.9 | PFind | NONE | 0.00 | 0.00 | NONE |
| 0.0000 | 67.2 | PFind | NONE | 0.00 | 0.00 | NONE |
| 0.0000 | 68.3 | PFind | NONE | 0.00 | 0.00 | NONE |
| 0.0000 | 63.5 | PFind | NONE | 0.00 | 0.00 | NONE |

FIG.8C

FILE: UNTITLED1

ID: SPT1189API
   COMMENT: B#70870AA001
SCAN TYPE: NORMAL
START ANGLE: 2 DEG.
STOP ANGLE: 40 DEG.
NUM POINTS: 1901
STEP SIZE: 0.02 DEG.
DATAFILE RES: 1600
SCAN RATE: 2.000000
SCAN MODE: CONTINUOUS
WAVELENGTH: 1.540562

DIFFRACTOMETER OPTICS:
   DETECTOR:
      TYPE: FIXED SLITS
      X2 CONFIGURATION: NO
   TUBE:
      TYPE: FIXED SLITS
      X2 CONFIGURATION: NO

FIG. 16A

PEAKS:

| POSITION | | ESD | CORR. FACT | INTENSITY | REL. INT. | FWHM (L) |
|---|---|---|---|---|---|---|
| (Deg.) | (DSp.) | (Deg.) | | (CPS) | (%) | |
| 4.3719 | 20.1948 | 0.0000 | 0.0000 | 1780.00 | 25.60 | 0.1600 |
| 7.1075 | 12.4269 | 0.0000 | 0.0000 | 265.14 | 3.81 | 0.0000 |
| 8.7675 | 10.0774 | 0.0000 | 0.0000 | 6952.43 | 100.00 | 0.1600 |
| 10.3594 | 8.5322 | 0.0000 | 0.0000 | 911.70 | 13.11 | 0.1600 |
| 11.0700 | 7.9860 | 0.0000 | 0.0000 | 2525.17 | 36.32 | 0.1600 |
| 12.2819 | 7.2006 | 0.0000 | 0.0000 | 725.77 | 10.44 | 0.1200 |
| 12.4456 | 7.1062 | 0.0000 | 0.0000 | 603.23 | 8.68 | 0.1600 |
| 13.1150 | 6.7450 | 0.0000 | 0.0000 | 497.17 | 7.16 | 0.1600 |
| 13.2463 | 6.6705 | 0.0000 | 0.0000 | 565.42 | 8.13 | 0.1000 |
| 13.9275 | 6.3533 | 0.0000 | 0.0000 | 3111.03 | 44.75 | 0.1600 |
| 15.2775 | 5.7948 | 0.0000 | 0.0000 | 1165.85 | 16.77 | 0.1600 |
| 16.5294 | 5.3586 | 0.0000 | 0.0000 | 518.88 | 7.46 | 0.1200 |
| 17.6975 | 5.0075 | 0.0000 | 0.0000 | 3406.78 | 49.00 | 0.1600 |
| 18.4606 | 4.8021 | 0.0000 | 0.0000 | 1104.02 | 15.88 | 0.1600 |
| 19.3144 | 4.5918 | 0.0000 | 0.0000 | 1370.93 | 19.72 | 0.1600 |
| 19.7819 | 4.4843 | 0.0000 | 0.0000 | 1433.98 | 20.34 | 0.1600 |
| 20.5200 | 4.3246 | 0.0000 | 0.0000 | 673.33 | 9.68 | 0.1600 |
| 20.8463 | 4.2577 | 0.0000 | 0.0000 | 584.72 | 8.41 | 0.1600 |
| 21.1300 | 4.2011 | 0.0000 | 0.0000 | 872.03 | 12.54 | 0.1600 |
| 21.5963 | 4.1115 | 0.0000 | 0.0000 | 1069.35 | 15.38 | 0.1600 |
| 22.1894 | 4.0029 | 0.0000 | 0.0000 | 1760.90 | 25.33 | 0.1200 |
| 23.2480 | 3.8228 | 0.0000 | 0.0000 | 1043.55 | 15.01 | 0.1600 |
| 23.5000 | 3.7825 | 0.0000 | 0.0000 | 430.00 | 6.18 | 0.1600 |
| 25.2075 | 3.5300 | 0.0000 | 0.0000 | 525.00 | 7.41 | 0.1400 |
| 25.6388 | 3.4716 | 0.0000 | 0.0000 | 450.63 | 6.48 | 0.1600 |
| 27.4406 | 3.2476 | 0.0000 | 0.0000 | 1330.93 | 19.14 | 0.1600 |
| 28.6437 | 3.1139 | 0.0000 | 0.0000 | 508.95 | 7.32 | 0.1600 |
| 29.3738 | 3.0301 | 0.0000 | 0.0000 | 582.17 | 8.37 | 0.1600 |
| 31.2800 | 2.8572 | 0.0000 | 0.0000 | 468.33 | 6.74 | 0.0800 |
| 32.0231 | 2.7926 | 0.0000 | 0.0000 | 732.08 | 10.53 | 0.1600 |
| 32.9000 | 2.7201 | 0.0000 | 0.0000 | 411.67 | 5.92 | 0.1600 |
| 35.8600 | 2.5021 | 0.0000 | 0.0000 | 429.17 | 6.17 | 0.1600 |
| 35.9400 | 2.4967 | 0.0000 | 0.0000 | 423.57 | 6.09 | 0.1200 |
| 36.5744 | 2.4548 | 0.0000 | 0.0000 | 782.05 | 11.25 | 0.1200 |

FIG. 16B

| ESD (Deg.) | AREA | SOURCE | CURVE | STRAIN | CSize | CSize SOURCE |
|---|---|---|---|---|---|---|
| 0.0000 | 284.8 | PFind | NONE | 0.00 | 0.00 | NONE |
| 0.0000 | 0.0 | Manual | NONE | 0.00 | 0.00 | NONE |
| 0.0000 | 1112.4 | PFind | NONE | 0.00 | 0.00 | NONE |
| 0.0000 | 145.9 | PFind | NONE | 0.00 | 0.00 | NONE |
| 0.0000 | 404.0 | PFind | NONE | 0.00 | 0.00 | NONE |
| 0.0000 | 116.1 | PFind | NONE | 0.00 | 0.00 | NONE |
| 0.0000 | 72.4 | PFind | NONE | 0.00 | 0.00 | NONE |
| 0.0000 | 79.6 | PFind | NONE | 0.00 | 0.00 | NONE |
| 0.0000 | 90.5 | PFind | NONE | 0.00 | 0.00 | NONE |
| 0.0000 | 497.8 | PFind | NONE | 0.00 | 0.00 | NONE |
| 0.0000 | 186.5 | PFind | NONE | 0.00 | 0.00 | NONE |
| 0.0000 | 83.0 | PFind | NONE | 0.00 | 0.00 | NONE |
| 0.0000 | 545.1 | PFind | NONE | 0.00 | 0.00 | NONE |
| 0.0000 | 176.6 | PFind | NONE | 0.00 | 0.00 | NONE |
| 0.0000 | 219.3 | PFind | NONE | 0.00 | 0.00 | NONE |
| 0.0000 | 226.2 | PFind | NONE | 0.00 | 0.00 | NONE |
| 0.0000 | 80.8 | PFind | NONE | 0.00 | 0.00 | NONE |
| 0.0000 | 93.6 | PFind | NONE | 0.00 | 0.00 | NONE |
| 0.0000 | 104.6 | PFind | NONE | 0.00 | 0.00 | NONE |
| 0.0000 | 171.1 | PFind | NONE | 0.00 | 0.00 | NONE |
| 0.0000 | 281.7 | PFind | NONE | 0.00 | 0.00 | NONE |
| 0.0000 | 167.0 | PFind | NONE | 0.00 | 0.00 | NONE |
| 0.0000 | 68.8 | PFind | NONE | 0.00 | 0.00 | NONE |
| 0.0000 | 51.5 | PFind | NONE | 0.00 | 0.00 | NONE |
| 0.0000 | 54.1 | PFind | NONE | 0.00 | 0.00 | NONE |
| 0.0000 | 186.3 | PFind | NONE | 0.00 | 0.00 | NONE |
| 0.0000 | 81.4 | PFind | NONE | 0.00 | 0.00 | NONE |
| 0.0000 | 93.1 | PFind | NONE | 0.00 | 0.00 | NONE |
| 0.0000 | 37.5 | PFind | NONE | 0.00 | 0.00 | NONE |
| 0.0000 | 117.1 | PFind | NONE | 0.00 | 0.00 | NONE |
| 0.0000 | 65.9 | PFind | NONE | 0.00 | 0.00 | NONE |
| 0.0000 | 68.7 | PFind | NONE | 0.00 | 0.00 | NONE |
| 0.0000 | 50.8 | PFind | NONE | 0.00 | 0.00 | NONE |
| 0.0000 | 125.1 | PFind | NONE | 0.00 | 0.00 | NONE |

CRYSTALLINE FORMS OF DOCETAXEL AND PROCESS FOR PREPARATION THEREOF

RELATED APPLICATIONS

This application is a divisional of U.S. patent application Ser. No. 11/975,511 which was filed with the U.S. Patent and Trademark Office on Oct. 19, 2007 now U.S. Pat. No. 7,662,980. Priority is claimed for this invention and application, corresponding applications having been filed in United States on United States on Oct. 20, 2006, No. 60/853,341 respectively.

BACKGROUND OF THE INVENTION

1. Field of the Invention

The present invention relates to novel crystalline forms of docetaxel and process for the preparation thereof.

2. Description of the Related Art

Docetaxel is a compound found to exhibit anti-tumor activity. It is presently sold under the trademark TAXOTERE®. While there are known techniques for synthesizing docetaxel, there is still a need for improved chemical processes which can produce this anti-cancer compound and in a form where the compound is chemically stable.

SUMMARY OF THE INVENTION

In accordance with the first aspect of the present invention, a novel crystalline anhydrous docetaxel characterized by a powder x-ray diffraction with peaks at about 8.0, 12.4, and 16.8±0.2 degrees two-theta is found.

Preferably, the novel crystalline anhydrous docetaxel is further characterized by a powder x-ray diffraction pattern with peaks at about 11.3, 13.8, 15.4, 20.3, and 23.3±0.2 degrees two-theta. More preferably, crystalline anhydrous docetaxel is further characterized by a powder x-ray diffraction pattern with peaks at about 4.6, 9.2, 18.1, 18.4, 19.5, 20.8, 22.5, 23.7, 24.1, 28.3, and 30.6 and ±0.2 degrees two-theta. The novel crystalline anhydrous docetaxel is preferably characterized by a powder x-ray diffraction pattern as substantially depicted in FIG. 3 or FIG. 4.

It is surprisingly found that the crystalline anhydrous form of docetaxel in accordance with the present invention is more stable than trihydrated form (see FIG. 2). The crystalline anhydrous form of docetaxel in accordance with the present invention in a therapeutically effective amount may be formulated with at least one pharmaceutically acceptable excipient to form a pharmaceutical composition. Such a composition may be administered to a mammal, such as human, to treat a proliferative disorder.

In accordance with the second aspect of the present invention, a process of producing a crystalline anhydrous docetaxel is provided. The process comprises (a) combining docetaxel and halohydrocarbon to form a solution; and (b) adding an antisolvent to the solution to precipitate the crystalline. The halohydrocarbon is preferably chlorohydrocarbon, more preferably, dichloromethane. The antisovlent may be C3-C8 linear or branched alkanes, preferably, n-heptane.

In accordance with the third aspect of the present invention, a process of producing docetaxel trihydrate is provided. The process comprises a) combining anhydrous docetaxel, and acetonitrile; b) heating the mixture of step a) to about 30-60° C.; c) adding water to the mixture of the heated mixture of step d); cooling the mixture of c) to about 10-30° C. to obtain a slurry; and e) filtering, washing, and drying the slurry of step d) to obtain docetaxel trihydrate.

The present application also provides a new process of synthesizing docetaxel and new crystalline docetaxel trihydrate as explained in detail below.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings:

FIG. 4 lists x-ray diffraction peaks for crystalline anhydrous docetaxel prepared in accordance with the process described in the present application.

FIGS. 6-7 shows an X-ray powder diffraction pattern of crystalline anhydrous docetaxel prepared in accordance with the process described in the present application.

FIG. 8 lists x-ray diffraction peaks for crystalline anhydrous docetaxel prepared in accordance with the process described in the present application.

FIG. 16 lists x-ray diffraction peaks for crystalline docetaxel trihydrate prepared in accordance with the process described in the present application.

DETAILED DESCRIPTION OF THE PRESENTLY PREFERRED EMBODIMENTS

Figure 1:
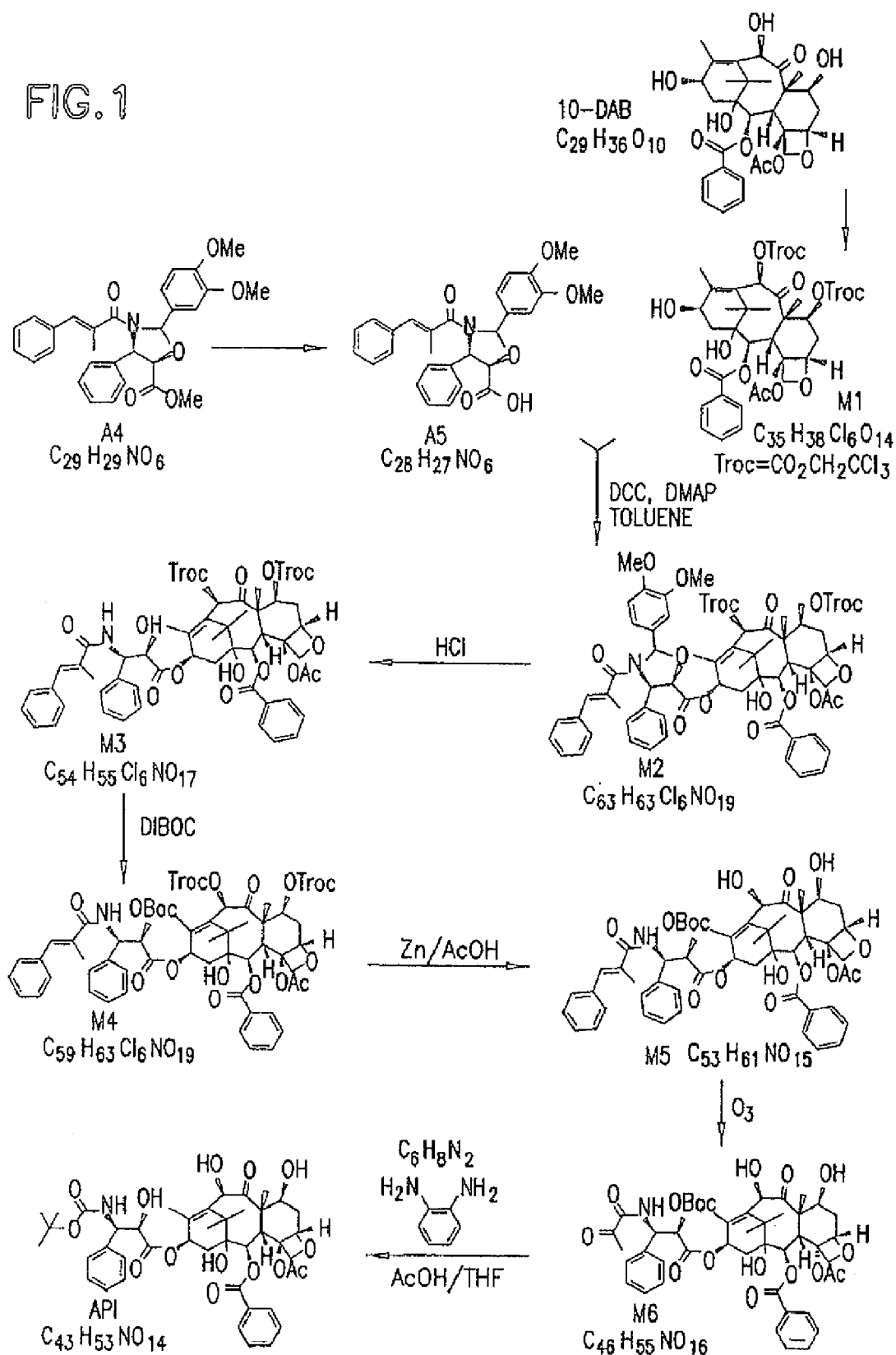
FIG. 1 shows a semisynthetic process of making docetaxel.
Figure 2A:
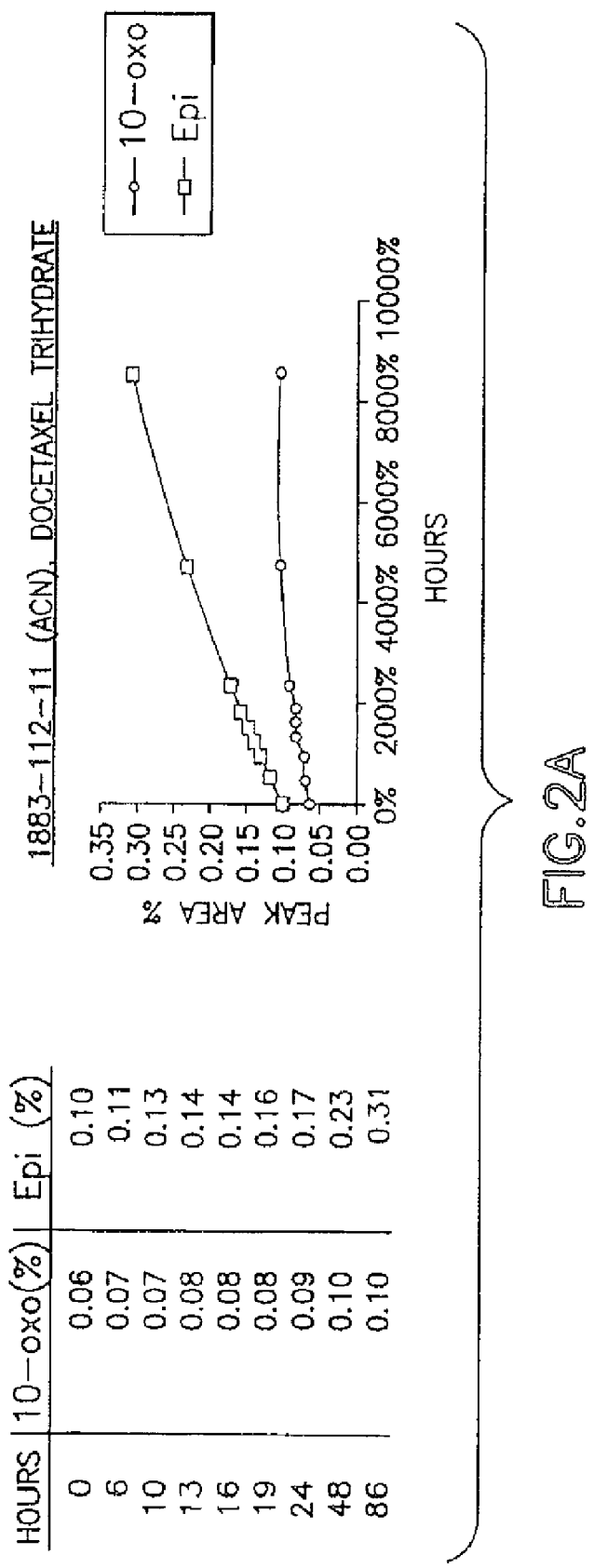
FIG. 2 illustrates the stability of crystalline anhydrous docetaxel and docetaxel trihydrate.
Figure 2B:
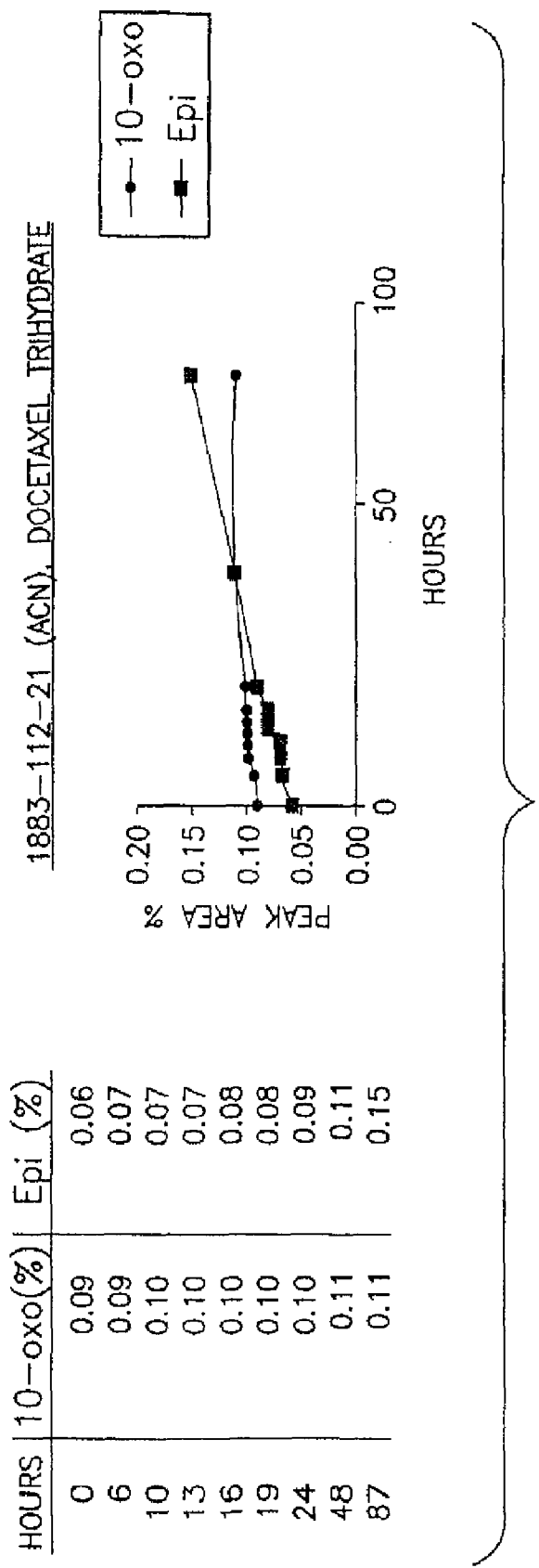
Figure 2C:
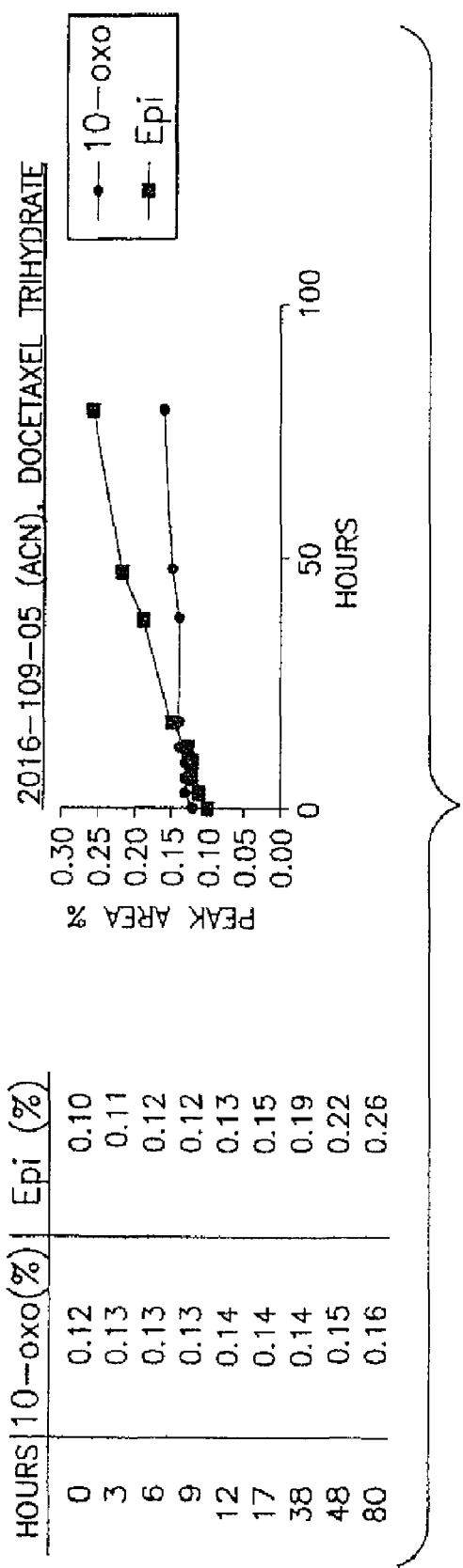
Figure 2E:
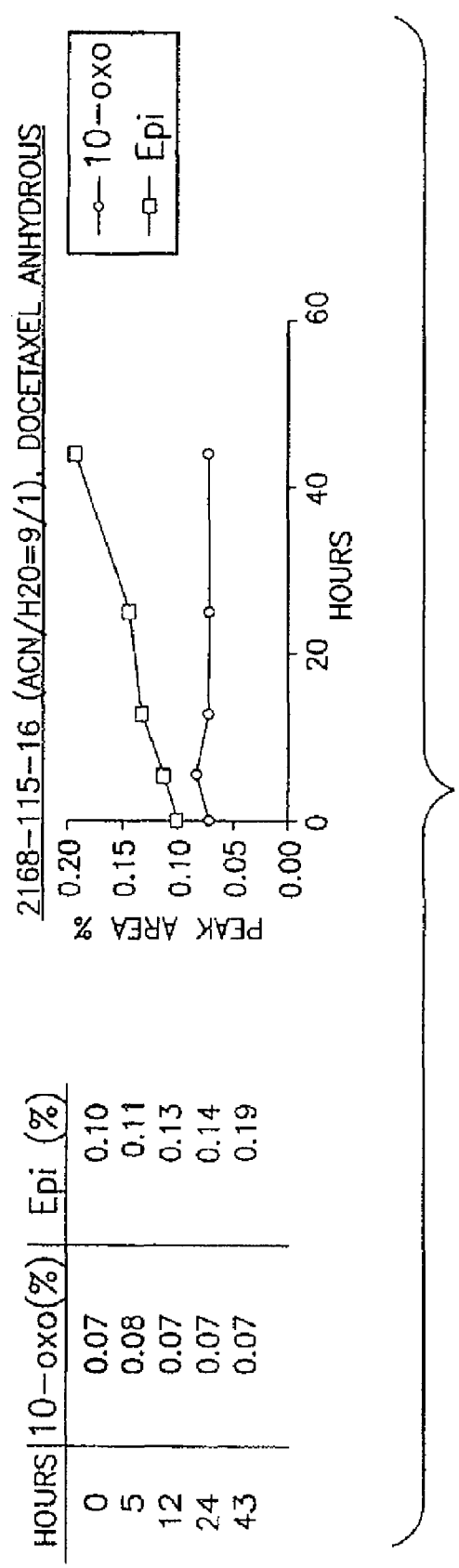

As an example, the semisynthetic process used to make docetaxel is outlined in the FIG. 1. This process comprise the synthesis of a certain oxazolidine (A-5) from (2R,3S)-3-phenylisoserine HCl as the starting material. 10-deacetyl-baccatin III that has 2,2,2-tri-chloroethoxy-carbonyl protecting groups in both the 7 and 10 positions (SPT1141-M1) is then esterified with the oxazolidine (A-5) in the presence of dicyclohexylcarbodiimide and 4-dimethylaminopyridine in toluene to produce an ester intermediate (SPT1141-M2). The ester intermediate is converted to docetaxel by a five-step procedure. Hydrochloric acid hydrolysis produces the β-amino ester (SPT1141-M3). T-butoxycarbonyl is attached to produce SPT1141-M4. The 2,2,2-tri-chloroethoxy-carbonyl protecting groups are removed by reacting SPT1141-M4 with zinc and acetic acid to produce SPT1141-M5. Further removal of protecting groups by reaction with ozone in methanol and subsequently by reaction with o-phenylenediamine and acetic acid in tetrahydrofuran produces crude docetaxel.

In the step described as Step 8a, Purification, the crude docetaxel is dissolved in ethyl acetate, filtered, concentrated under vacuum to produce a residue, dichloromethane is added to dissolve the residue and the solution is purified by chromatography with acetone and n-heptane as the eluant. The purified solution is concentrated under vacuum and the docetaxel is obtained by filtering.

In Step 8b, recrystallization—anhydrous, the purified docetaxel is dissolved in dichloromethane, n-heptane is added and the solution is seeded with docetaxel seed. The solution is cooled and the resulting slurry is filtered and the wet cake is dried to provide anhydrous docetaxel. The resulting anhydrous docetaxel can be further converted to the trihydrate form in Step 8c, recrystallization (trihydrate form) by mixing the anhydrous docetaxel with acetonitrile and glacial acetic acid, adding water at a temperature between 30 to 50° C., then adding more water and seeding with docetaxel seed. The resulting slurry is then filtered and washed with water and the wet cake is dried under vacuum at 60° C. to provide docetaxel trihydrate.

We surprisingly found that the anhydrous form of docetaxel is more stable (2168-115-16) than trihydrated form (1883-12-11, 1883-12-21, 2016-109-05) in acetonitrile. See FIG. 2. Also, the anhydrous form is more stable in acetonitrile than in acetonitrile/water (9/1). These data showed that docetaxel is less stable in co-water solvent. Docetaxel is more stable in non-water solvent than co-water solvent (ACN/water/acetic acid). Further more, an impurity of docetaxel, 7-epi-docetaxel, is generated more rapidly in co-water solvent than in non-water solvent. The growth of 7-epi-docetaxel can be suppressed by the addition of acetic acid.

More detailed description of each step of the process shown in FIG. 2 is provided below.

Step 1: Protection

10-Deacetyl baccatin III (approx. 14 Kg), pyridine (approx. 137 Kg), and 2,2,2-trichloroethyl chloroformate (approx. 14 Kg) are charged into a suitable vessel. The resulting mixture is stirred at not more than (NMT) 10° C. After the reaction is complete, the solution is quenched with water followed by extraction with dichloromethane; the organic layer is separated and washed with water. The organic layer is concentrated at NMT 60° C., and water is added for precipitation. The solids are collected and washed with water. The wet cake is then suspended in ethyl acetate and heptanes are added. The solids are isolated, washed, and dried under vacuum at NMT 60° C. to provide SPT1141 M1 (approx. 22 Kg).

Step 2-1: Hydrolysis

SPT2039 A4 (approx. 2.7 Kg), tetrahydrofuran (approx. 11 Kg), and about 1 N lithium hydroxide solution (approx. 6.6 Kg) are charged into a suitable vessel. The mixture is stirred. After the reaction is complete, toluene and hydrochloric acid are added to adjust the mixture to pH<3. The organic layer is washed with sodium chloride solution, and magnesium sulfate is added to remove water. The filtrate is concentrated to provide SPT2039 A5 in toluene solution, and the mixture is used directly in the next step.

Step 2-2: Coupling Reaction

SPT1141 M1 (approx. 3.8 Kg), toluene (approx. 11 Kg), 4-dimethyiaminopyridjne (approx. 114 g), and I,$^3$-dicyclohexylcarbondiimide (approx. 1.3 Kg) are added to the mixture from step 2-1The reaction mixture is stirred. After the reaction is complete, the reaction mixture is quenched with hydrochloric acid. The slurry is filtered, and the filtrate is collected and separated. The organic layer is washed with sodium bicarbonate solution followed by water. The organic phase is concentrated to provide SPT11141 M2 in toluene solution, and the mixture is used directly in the next step.

Step 3: Deprotection

Tetrahydrofuran (approx. 21 Kg) is added to the above mixture. The solution is cooled to NMT 10° C., and a solution of hydrochloric acid in methanol is slowly added. The mixture is stirred at below 40° C. until the reaction is complete. Ethyl acetate and sodium bicarbonate solution are then added to the resulting mixture. The organic layer is collected and washed with sodium chloride solution. After concentration, SPT1141 M3 is dissolved in ethyl acetate, and the solution is used directly in the next step.

Step 4: BOC protection

Dl-tert-butyl dicarbonate (approx. 1 Kg) is charged into a suitable vessel containing a solution of 4-dimethylaminopyridine (approx. 15 g) in SPT1141 M3 solution. After the reaction is complete,~the solution is quenched with diluted hydrochloric acid, and sodium chloride solution is added. The organic layer is concentrated, and tetrahydrofuran is added to provide SPT1141 M4 solution. The solution is used directly in the next step.

Step 5: Deprotection

Zinc (approx. 2.7 Kg), glacial acetic acid (approx. 10.8 Kg), tetrahydrofuran, and SPT1141 M4 solution are charged into a suitable vessel. After the reaction is complete, the mixture is filtered, and the filtrate is solvent swapped with isopropanol. Water is added to the resulting solution. The solids are filtered and washed to provide crude SPT1141 M5 (approx. 4 Kg).

Crude SPT1141 M5 (approx. 4 Kg) and dichloromethane (approx. 54 Kg) are charged into a suitable vessel. The solution is extracted with sodium chloride solution. Glacial acetic acid is added to the organic layer. The mixture is then concentrated and heptanes is added for crystallization. The solids are filtered, washed and dried to provide SPT1141 M5 (approx. 3.3 Kg).

Step 6: Ozonolysis

Ozone is added at NMT −40° C. to a suitable vessel containing a mixture of SPT1141 M5 (approx. 5.5 Kg), methanol (approx. 88 Kg), and glacial acetic acid (approx. 55 g) while maintaining the temperature at NMT −40° C. After the reaction is complete, dimethyl sulfide are added while maintaining the temperature at NMT −40° C., and the mixture is warmed to 20 to 30° C. The mixture is concentrated, and water is added for precipitation. The solids are filtered, washed, and dried to provide SPT1141 M6 (approx. 4.6 Kg).

Step 7: Condensation

Glacial acetic acid (approx. 5 Kg) is charged into a suitable vessel containing a solution of SPT1141 M6 (approx. 4.6 Kg) and 1,2-phenylenedjamine (approx. 1.8 Kg) in tetrahydrofuran (approx. 110 Kg). The mixture Is then reacted under air at NMT 60° C., and 1,2-phenylenediamine is added. After the reaction is complete,° the reaction mixture is concentrated and solvent swapped with methanol at NMT 60° C. The solid by-products are removed, and the filtrate is mixed with a solution of hydrochloric acid. The solids are isolated, washed, and dried to provide crude docetaxel" (approx. 4 Kg).

Step 8a: Purification

Crude docetaxel (approx. 3 Kg) arid ethyl acetate (approx. 41 Kg) are charged into a suitable vessel. The mixture is stirred at NMT 60° C. and is filtered through a filter bed pie-coated with Celite, activated carbon, and activated acidic day. The filter bed is washed with ethyl acetate, and the filtrate is collected and concentrated under vacuum at NMT 60° C. until the volume of residue is approx. 9 L Dichloromethane is then charged to the residue to provide crude docetaxel solution (for column chromatography).

Step 8b: Recrystallization—Anhydrous Form

Docetaxel for crystallization (about 1 Kg) and dichioromethane are charge into a suitable vessel. The mixture is stirred at NMT 45° C. until the solid is dissolved, and n-heptane is added for crystallization. The slurry is filtered, washed, and dried to provide approx. 0.8 kg of docetaxel anhydrous. The solid" is then used for the trihydrate formation.

Step 8c: Recrystallization (Docetaxel Trihydrate)

Docetaxel anhydrous (about 0.8 Kg), acetonitrile (about 3.8 Kg) and glacial acetic acid (about 7.6 g) are charged into a suitable vessel. The mixture is heated to NMT 45° C., and purified process water (about 9.6 Kg) is added for precipitation. The slurry is filtered, washed and dried under a moist environment to provide docetaxel trihydrate (about 0.7 Kg).

Figure 5:
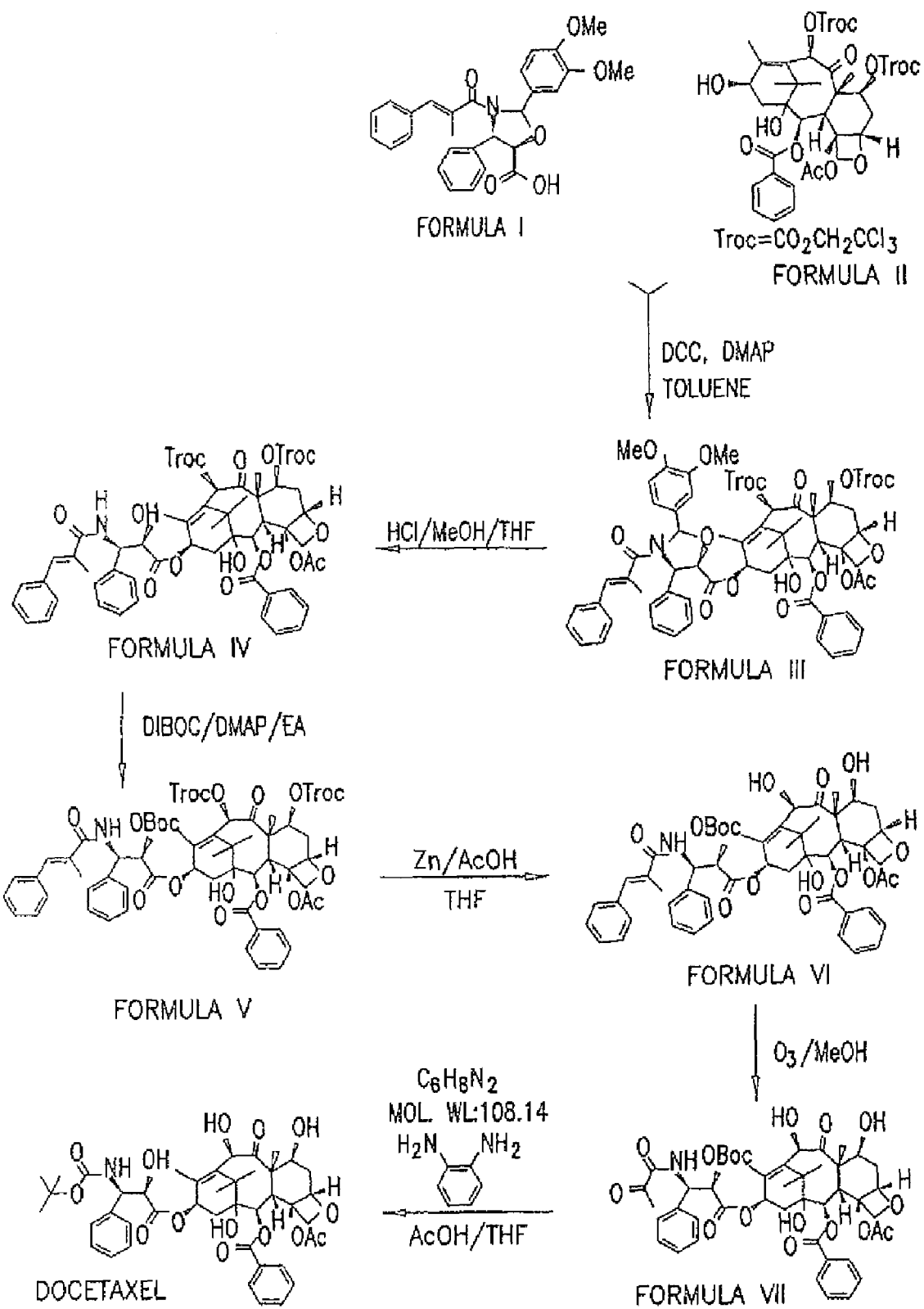
FIG. 5 also shows a semisynthetic process of making docetaxel.
Figure 6:
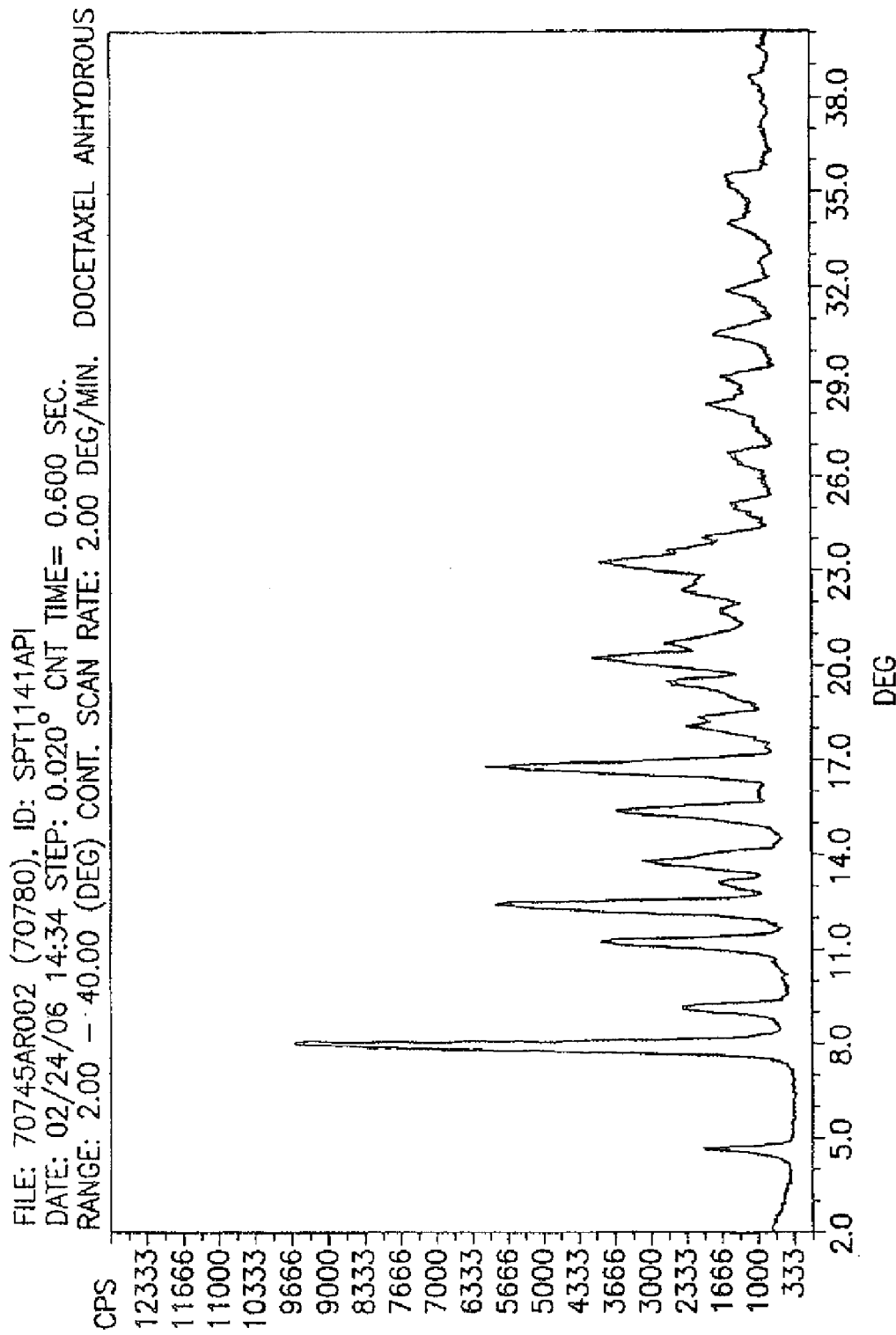
Figure 9:
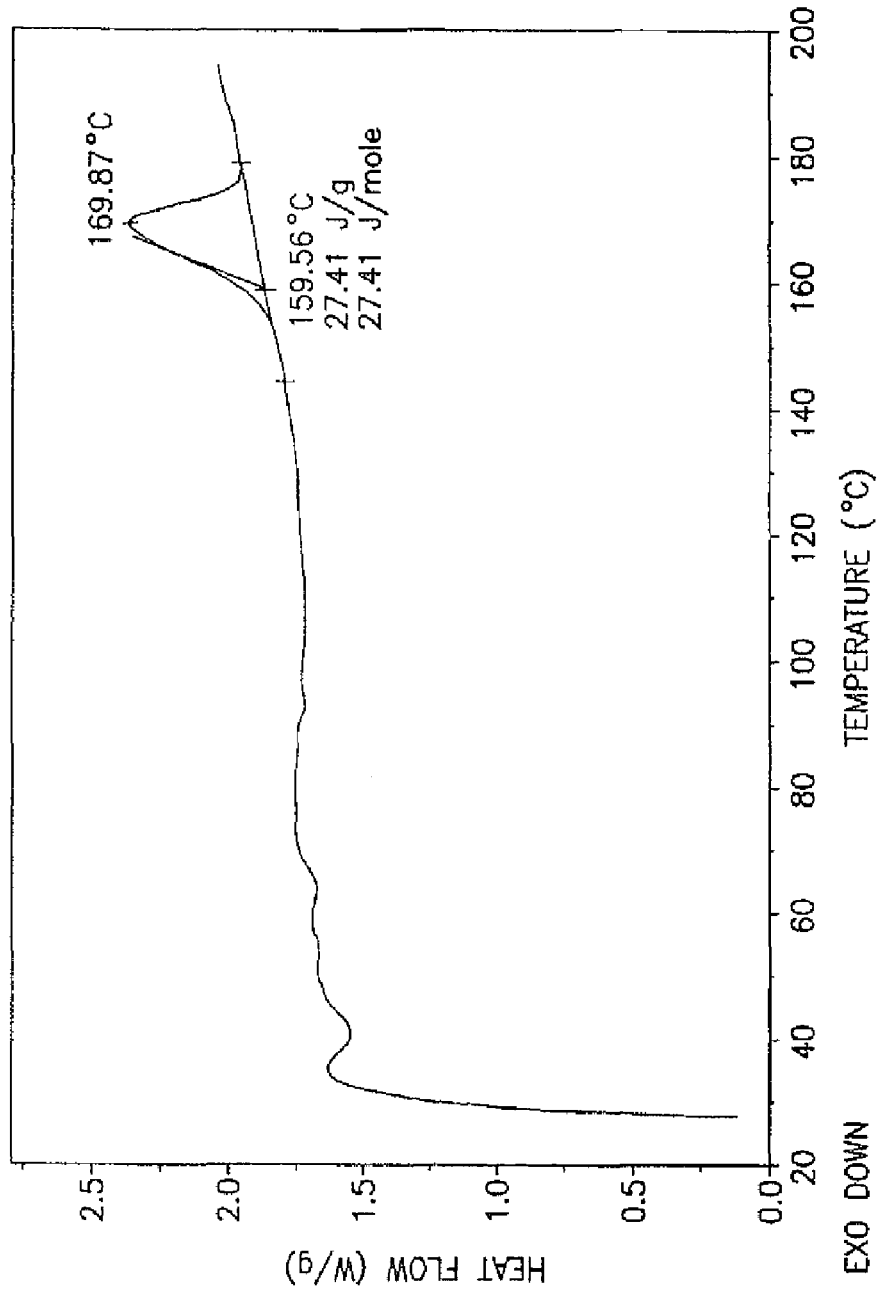
FIG. 9 shows DSC pattern of crystalline anhydrous docetaxel prepared in accordance with the process described in the present application.

FIG. 5 also illustrates a semisynthetic process used to make docetaxel.

The invention is not limited by the embodiments described above which are presented as examples only but can be modified in various ways within the scope of protection defined by the appended patent claims.

We claim:

1. Crystalline anhydrous N-debenzoyl-N-tert-butoxycarbonyl-10-deacetyl taxol characterized by a powder x-ray diffraction pattern with peaks at 8.0, 11.3, 12.4, 13.8 15.4, 16.8, 20.3, and 23.3 ±0.2 degrees two-theta.

2. The crystalline anhydrous N-debenzoyl-N-tert-butoxycarbonyl-10-deacetyl taxol of claim 1 further characterized by a powder x-ray diffraction pattern with peaks at 4.6, 9.2, 18.1, 18.4, 19.5, 20.8, 22.5, 23.7, 24.1, 28.3, and 30.6 ±0.2 degrees two-theta.

Figure 3:
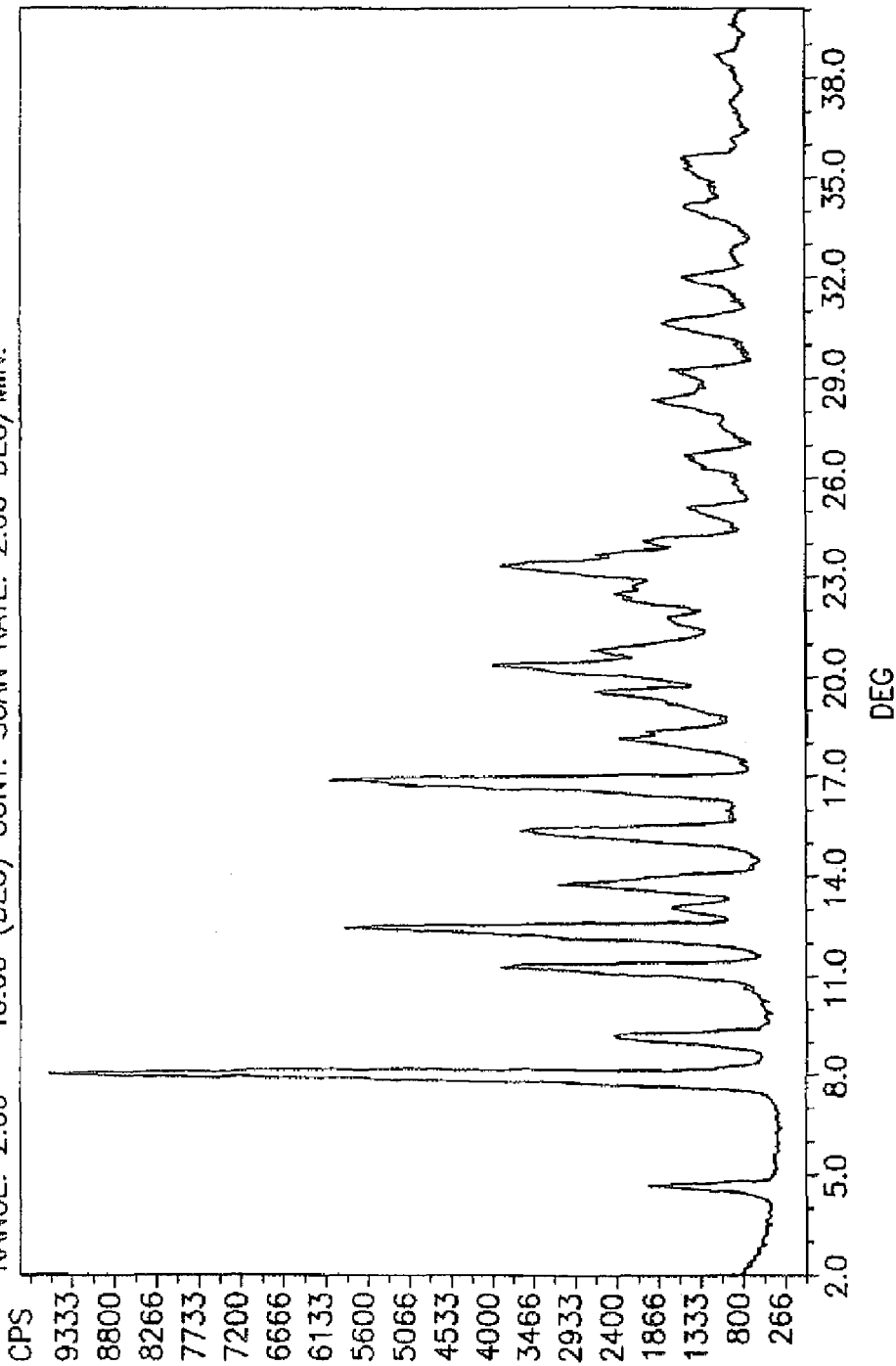
FIG. 3 shows an X-ray powder diffraction pattern of crystalline anhydrous docetaxel prepared in accordance with the process described in the present application.

3. The crystalline anhydrous N-debenzoyl-N-tert-butoxycarbonyl-10-deacetyl taxol of claim 1 characterized by a powder x-ray diffraction pattern as substantially depicted in FIG. 3.

4. The crystalline anhydrous N-debenzoyl-N-tert-butoxycarbonyl-10-deacetyl taxol of claim 1 characterized by a powder x-ray diffraction pattern as substantially depicted:

| PEAKS: | | | | | | |
|---|---|---|---|---|---|---|
| POSITION | | ESD | CORR. | INTENSITY | REL. INT. | FWHM |
| (Deg.) | (DSp.) | (Deg.) | FACT | (CPS) | (%) | (L) |
| 4.3719 | 20.1948 | 0.0000 | 0.0000 | 1780.00 | 25.60 | 0.1600 |
| 7.1075 | 12.4269 | 0.0000 | 0.0000 | 265.14 | 3.81 | 0.0000 |
| 8.7675 | 10.0774 | 0.0000 | 0.0000 | 6952.43 | 100.00 | 0.1600 |
| 10.3594 | 8.5322 | 0.0000 | 0.0000 | 911.70 | 13.11 | 0.1600 |
| 11.0700 | 7.9860 | 0.0000 | 0.0000 | 2525.17 | 36.32 | 0.1600 |
| 12.2819 | 7.2006 | 0.0000 | 0.0000 | 725.77 | 10.44 | 0.1200 |
| 12.4456 | 7.1062 | 0.0000 | 0.0000 | 603.23 | 8.68 | 0.1600 |
| 13.1150 | 6.7450 | 0.0000 | 0.0000 | 497.17 | 7.16 | 0.1600 |
| 13.2463 | 6.6705 | 0.0000 | 0.0000 | 565.42 | 8.13 | 0.1000 |
| 13.9275 | 6.3533 | 0.0000 | 0.0000 | 3111.03 | 44.75 | 0.1600 |
| 15.2775 | 5.7948 | 0.0000 | 0.0000 | 1165.85 | 16.77 | 0.1600 |
| 16.5294 | 5.3586 | 0.0000 | 0.0000 | 518.88 | 7.46 | 0.1200 |
| 17.6975 | 5.0075 | 0.0000 | 0.0000 | 3406.78 | 49.00 | 0.1600 |
| 18.4606 | 4.8021 | 0.0000 | 0.0000 | 1104.02 | 15.88 | 0.1600 |
| 19.3144 | 4.5918 | 0.0000 | 0.0000 | 1370.93 | 19.72 | 0.1600 |
| 19.7819 | 4.4843 | 0.0000 | 0.0000 | 1433.98 | 20.34 | 0.1600 |
| 20.5200 | 4.3246 | 0.0000 | 0.0000 | 673.33 | 9.68 | 0.1600 |
| 20.8463 | 4.2577 | 0.0000 | 0.0000 | 584.72 | 8.41 | 0.1600 |
| 21.1300 | 4.2011 | 0.0000 | 0.0000 | 872.03 | 12.54 | 0.1600 |
| 21.5963 | 4.1115 | 0.0000 | 0.0000 | 1069.35 | 15.38 | 0.1600 |
| 22.1894 | 4.0029 | 0.0000 | 0.0000 | 1760.90 | 25.33 | 0.1200 |
| 23.2480 | 3.8228 | 0.0000 | 0.0000 | 1043.55 | 15.01 | 0.1600 |
| 23.5000 | 3.7825 | 0.0000 | 0.0000 | 430.00 | 6.18 | 0.1600 |
| 25.2075 | 3.5300 | 0.0000 | 0.0000 | 525.00 | 7.41 | 0.1400 |
| 25.6388 | 3.4716 | 0.0000 | 0.0000 | 450.63 | 6.48 | 0.1600 |
| 27.4406 | 3.2476 | 0.0000 | 0.0000 | 1330.93 | 19.14 | 0.1600 |
| 28.6437 | 3.1139 | 0.0000 | 0.0000 | 508.95 | 7.32 | 0.1600 |
| 29.3738 | 3.0301 | 0.0000 | 0.0000 | 582.17 | 8.37 | 0.1600 |
| 31.2800 | 2.8572 | 0.0000 | 0.0000 | 468.33 | 6.74 | 0.0800 |
| 32.0231 | 2.7926 | 0.0000 | 0.0000 | 732.08 | 10.53 | 0.1600 |
| 32.9000 | 2.7201 | 0.0000 | 0.0000 | 411.67 | 5.92 | 0.1600 |
| 35.8600 | 2.5021 | 0.0000 | 0.0000 | 429.17 | 6.17 | 0.1600 |
| 35.9400 | 2.4967 | 0.0000 | 0.0000 | 423.57 | 6.09 | 0.1200 |
| 36.5744 | 2.4548 | 0.0000 | 0.0000 | 782.05 | 11.25 | 0.1200 |

| ESD (Deg.) | AREA | SOURCE | CURVE | STRAIN | CSize | CSize SOURCE |
|---|---|---|---|---|---|---|
| 0.0000 | 284.8 | PFind | NONE | 0.00 | 0.00 | NONE |
| 0.0000 | 0.0 | Manual | NONE | 0.00 | 0.00 | NONE |
| 0.0000 | 1112.4 | PFind | NONE | 0.00 | 0.00 | NONE |
| 0.0000 | 145.9 | PFind | NONE | 0.00 | 0.00 | NONE |
| 0.0000 | 404.0 | PFind | NONE | 0.00 | 0.00 | NONE |
| 0.0000 | 116.1 | PFind | NONE | 0.00 | 0.00 | NONE |
| 0.0000 | 72.4 | PFind | NONE | 0.00 | 0.00 | NONE |
| 0.0000 | 79.6 | PFind | NONE | 0.00 | 0.00 | NONE |
| 0.0000 | 90.5 | PFind | NONE | 0.00 | 0.00 | NONE |
| 0.0000 | 497.8 | PFind | NONE | 0.00 | 0.00 | NONE |
| 0.0000 | 186.5 | PFind | NONE | 0.00 | 0.00 | NONE |
| 0.0000 | 83.0 | PFind | NONE | 0.00 | 0.00 | NONE |
| 0.0000 | 545.1 | PFind | NONE | 0.00 | 0.00 | NONE |
| 0.0000 | 176.6 | PFind | NONE | 0.00 | 0.00 | NONE |
| 0.0000 | 219.3 | PFind | NONE | 0.00 | 0.00 | NONE |
| 0.0000 | 226.2 | PFind | NONE | 0.00 | 0.00 | NONE |
| 0.0000 | 80.8 | PFind | NONE | 0.00 | 0.00 | NONE |
| 0.0000 | 93.6 | PFind | NONE | 0.00 | 0.00 | NONE |
| 0.0000 | 104.6 | PFind | NONE | 0.00 | 0.00 | NONE |
| 0.0000 | 171.1 | PFind | NONE | 0.00 | 0.00 | NONE |
| 0.0000 | 281.7 | PFind | NONE | 0.00 | 0.00 | NONE |
| 0.0000 | 167.0 | PFind | NONE | 0.00 | 0.00 | NONE |
| 0.0000 | 68.8 | PFind | NONE | 0.00 | 0.00 | NONE |
| 0.0000 | 51.5 | PFind | NONE | 0.00 | 0.00 | NONE |
| 0.0000 | 54.1 | PFind | NONE | 0.00 | 0.00 | NONE |
| 0.0000 | 186.3 | PFind | NONE | 0.00 | 0.00 | NONE |
| 0.0000 | 81.4 | PFind | NONE | 0.00 | 0.00 | NONE |
| 0.0000 | 93.1 | PFind | NONE | 0.00 | 0.00 | NONE |
| 0.0000 | 37.5 | PFind | NONE | 0.00 | 0.00 | NONE |
| 0.0000 | 117.1 | PFind | NONE | 0.00 | 0.00 | NONE |
| 0.0000 | 65.9 | PFind | NONE | 0.00 | 0.00 | NONE |
| 0.0000 | 68.7 | PFind | NONE | 0.00 | 0.00 | NONE |
| 0.0000 | 50.8 | PFind | NONE | 0.00 | 0.00 | NONE |
| 0.0000 | 125.1 | PFind | NONE | 0.00 | 0.00 | NONE. |

5. The crystalline anhydrous N-debenzoyl-N-tert-butoxycarbonyl-10-deacetyl taxol of claim 1 further characterized by an infrared spectrum having bands at about 710, 1248, 1723, 2978, and 3430 (cm$^{-1}$).

Figure 10:
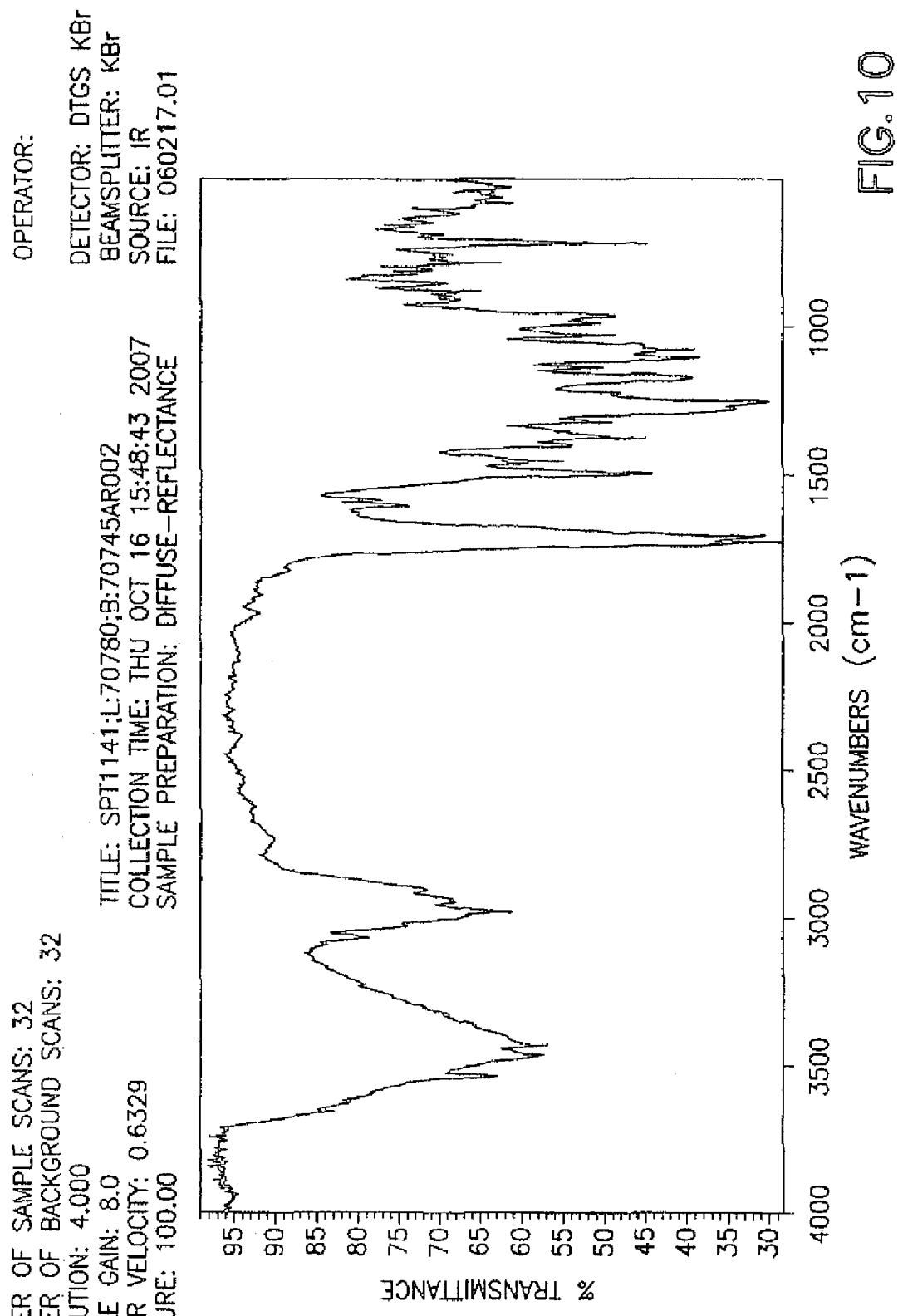
FIGS. 10-13 show IR pattern of crystalline anhydrous docetaxel prepared in accordance with the process described in the present application.
Figure 11:
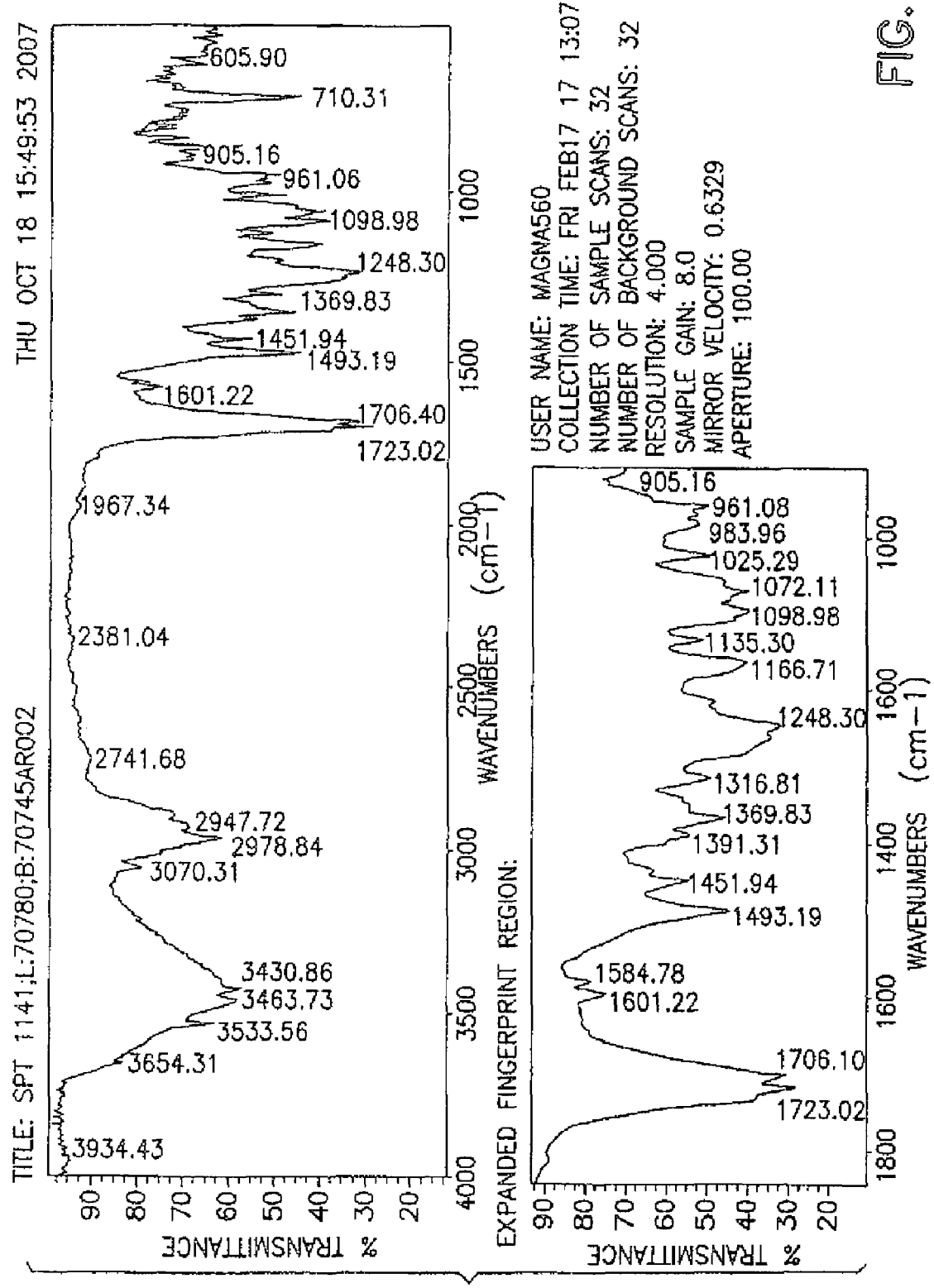
Figure 12:
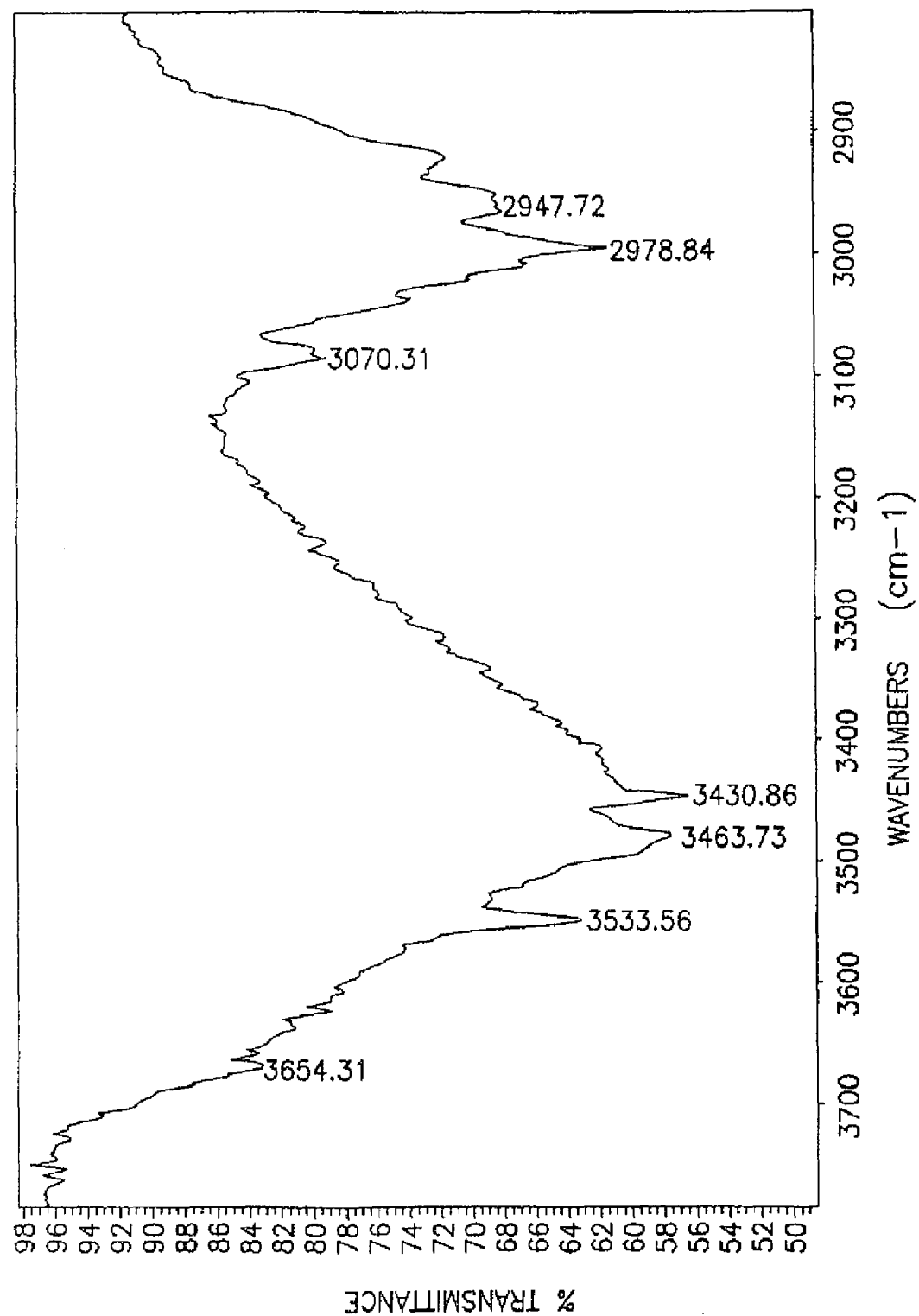
Figure 13:
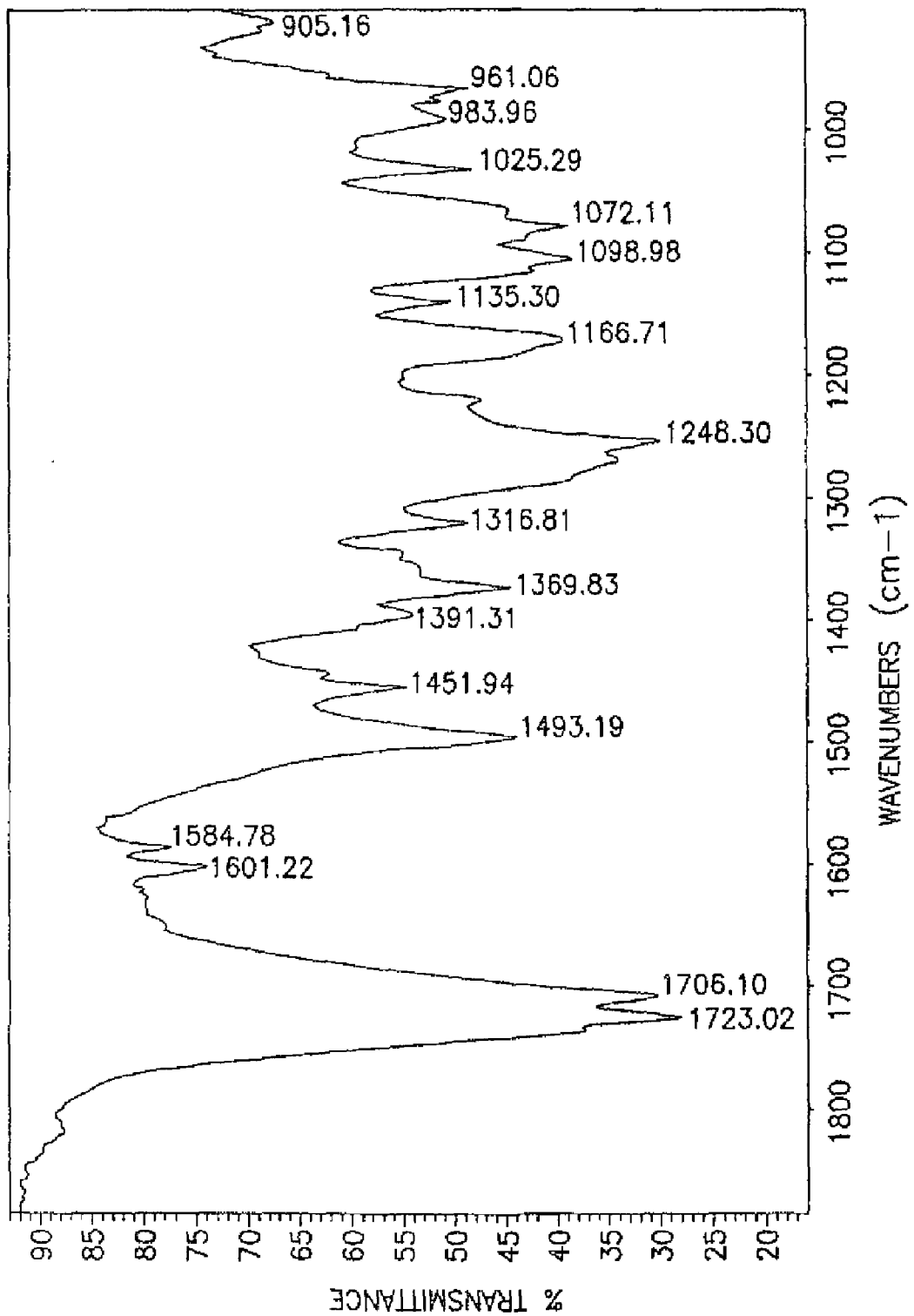
Figure 14:
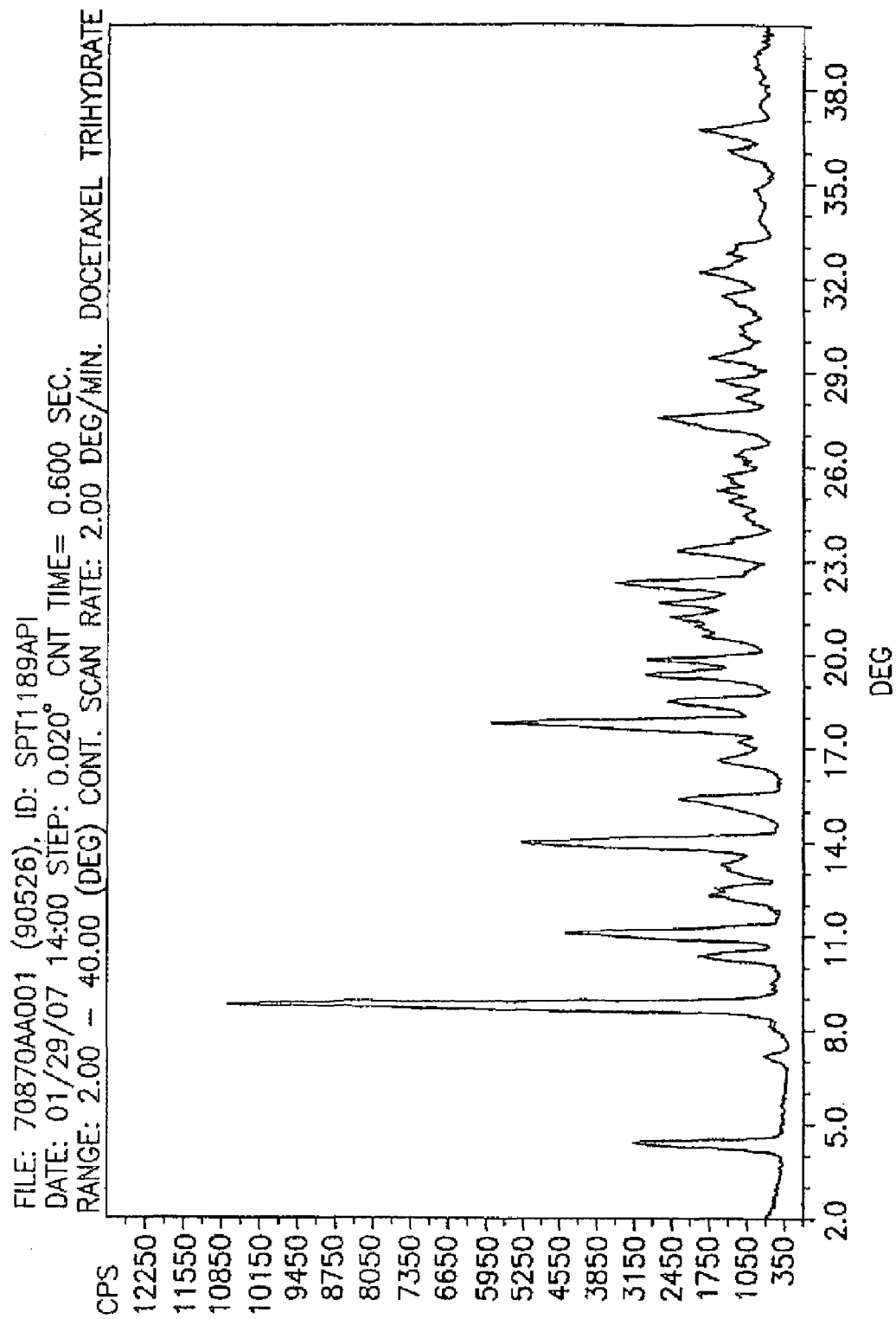
FIGS. 14-15 shows an X-ray powder diffraction pattern of crystalline docetaxel trihydrate prepared in accordance with the process described in the present application.
Figure 15:
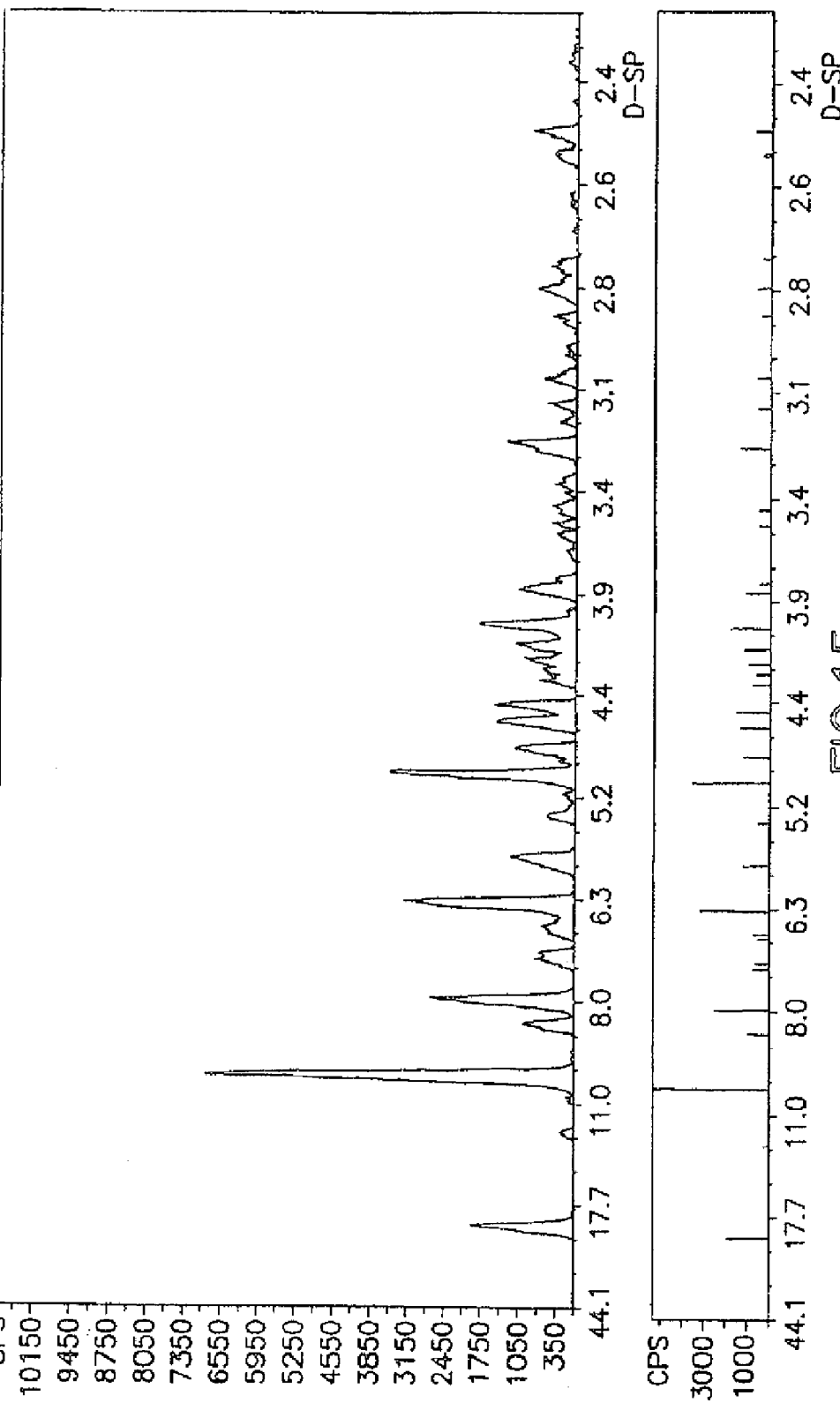
Figure 17:
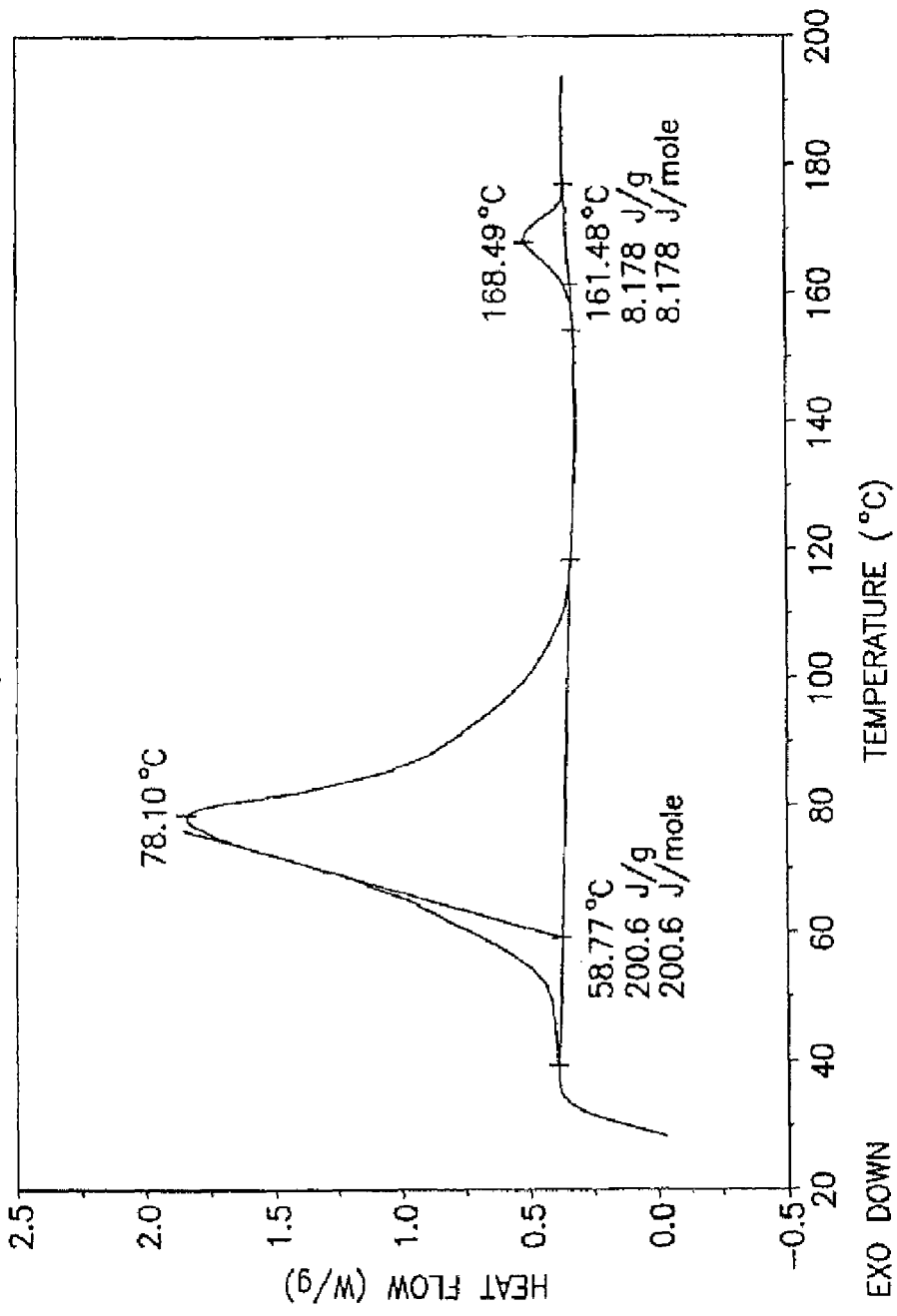
FIG. 17 shows DSC pattern of crystalline docetaxel trihydrate prepared in accordance with the process described in the present application.
Figure 18:
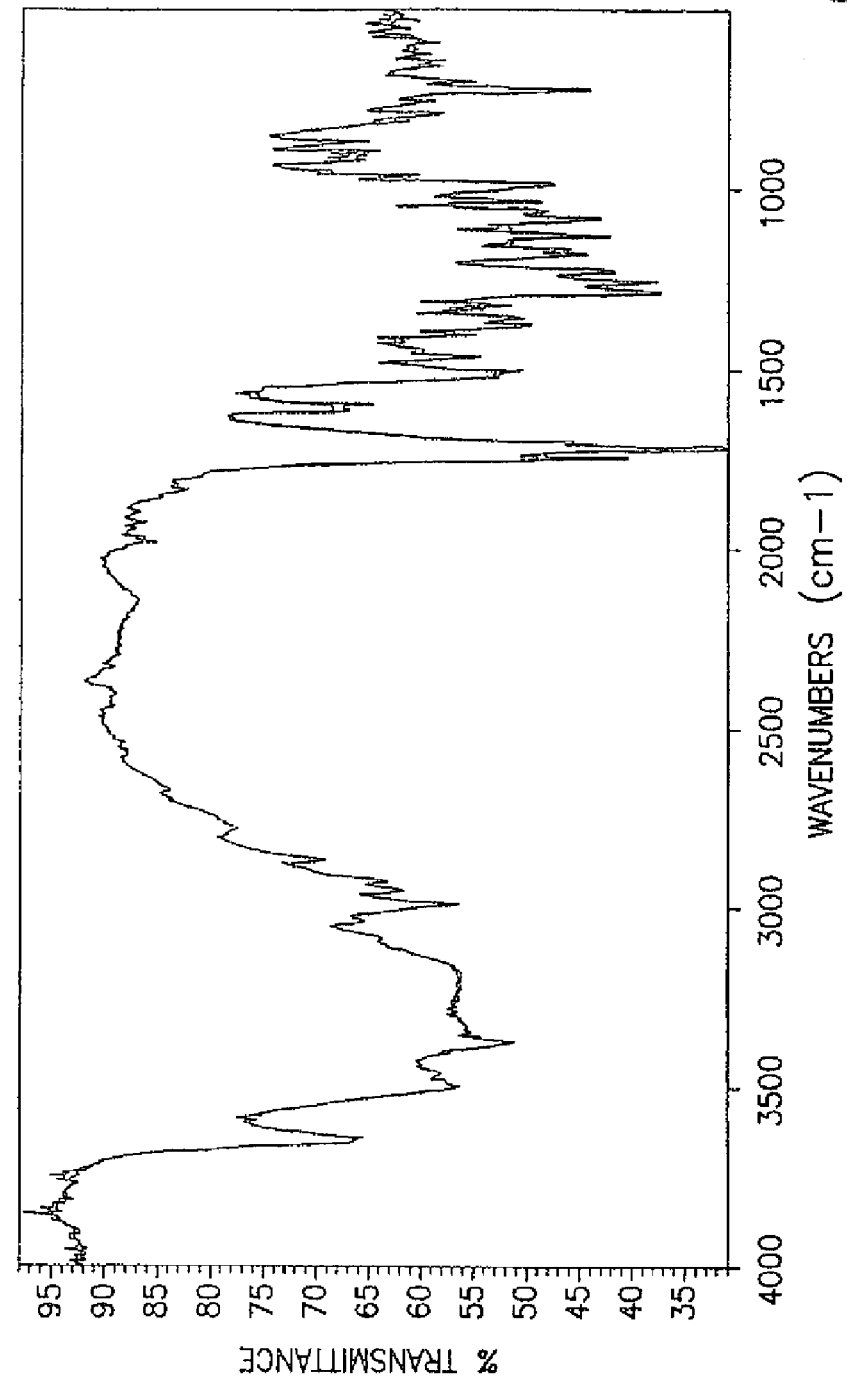
FIGS. 18-21 show IR pattern of crystalline docetaxel trihydrate prepared in accordance with the process described in the present application.
Figure 19:
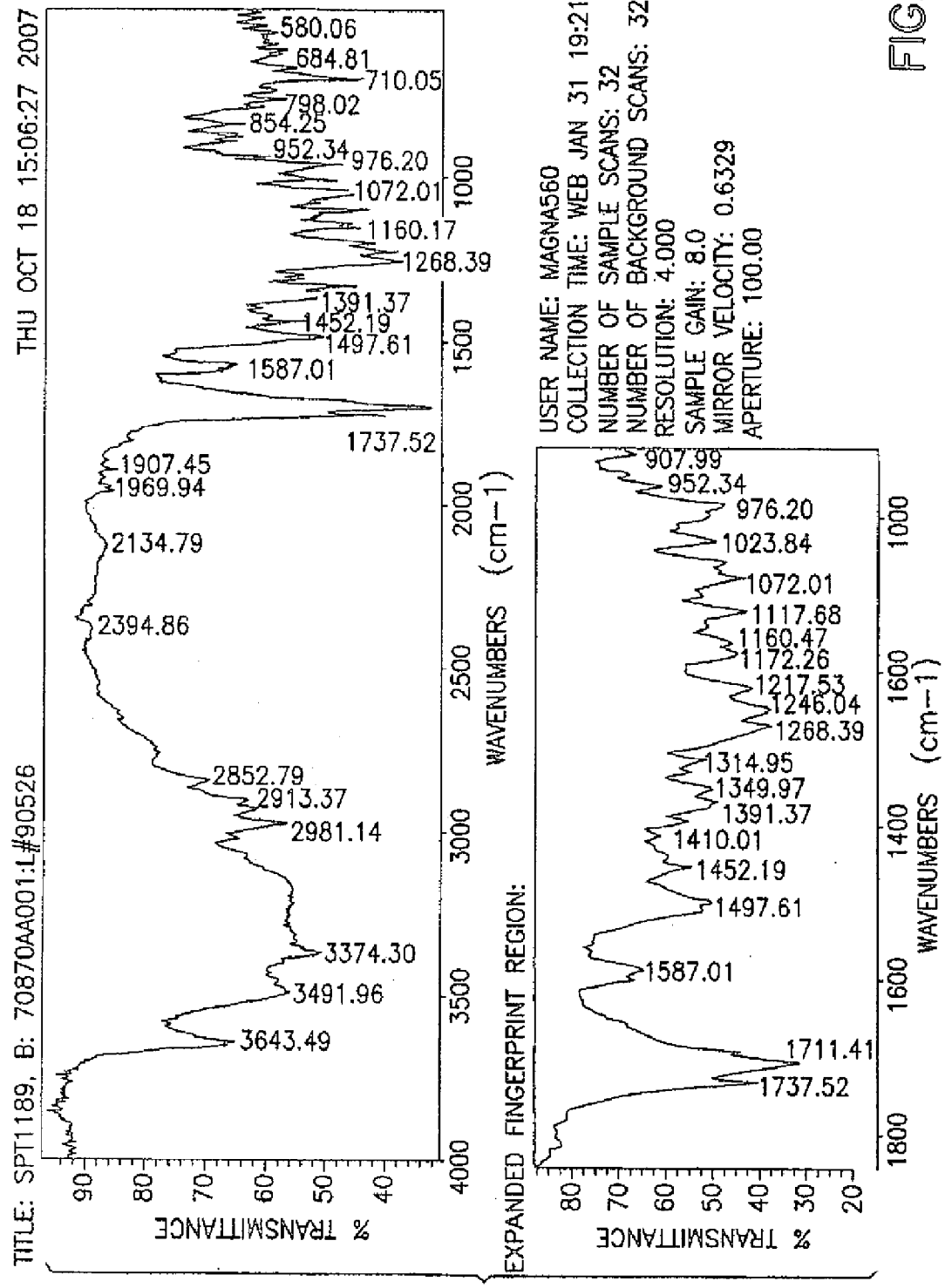
Figure 20:
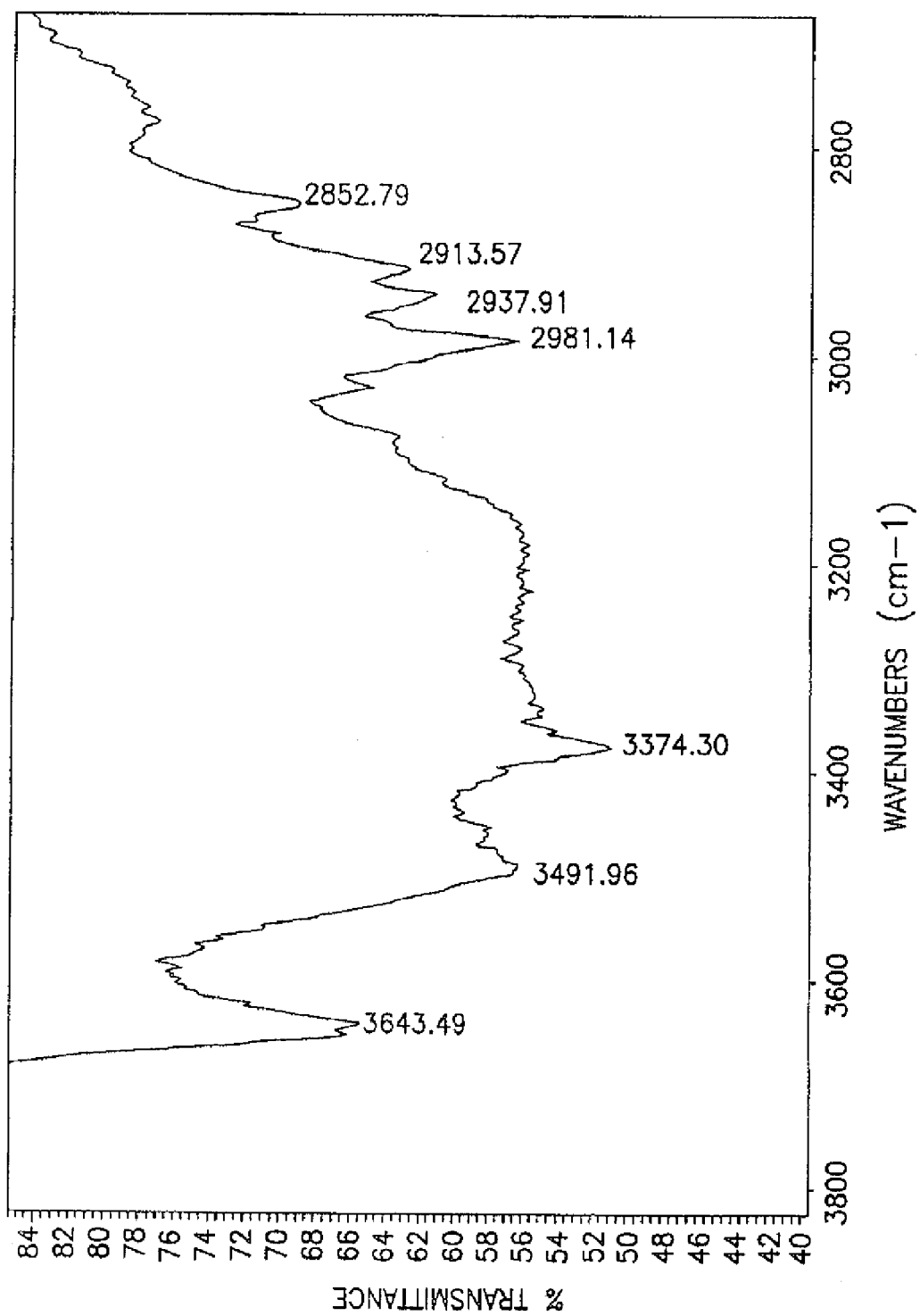
Figure 21:
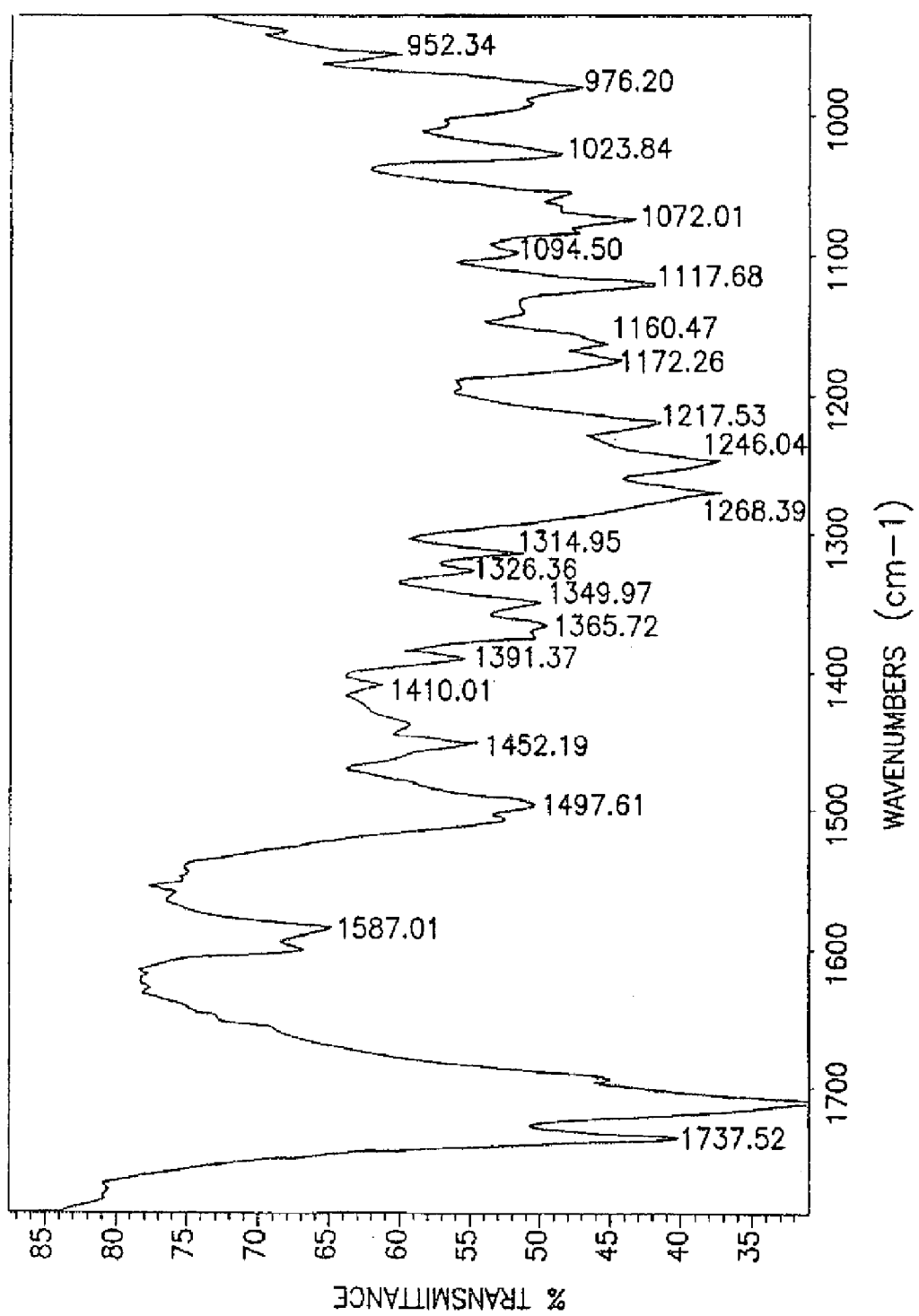

6. The crystalline anhydrous N-debenzoyl-N-tert-butoxycarbonyl-10-deacetyl taxol of claim 1 further characterized by an infrared spectrum as substantially depicted in FIG. 10.

* * * * *

(12) EX PARTE REEXAMINATION CERTIFICATE (10083rd)
United States Patent
Liao et al.

(10) Number: US 8,357,811 C1
(45) Certificate Issued: *Mar. 21, 2014

(54) CRYSTALLINE FORMS OF DOCETAXEL AND PROCESS FOR PREPARATION THEREOF

(75) Inventors: Yuan-Xiu Liao, Kaohsiung (TW); Meng-Fen Ho, Anding Township, Tainan County (TW); Shu-Ping Chen, Kaohsiung (TW); Chia-Ning Lin, Pingtung (TW); Yu-Li Lin, Yongkang (TW); Tsung-Yu Hsiao, Neimen Township, Kaohsiung County (TW)

(73) Assignee: ScinoPharm Singapore PTE Ltd., Singapore (SG)

Reexamination Request:
No. 90/012,941, Aug. 15, 2013

Reexamination Certificate for:
Patent No.: 8,357,811
Issued: Jan. 22, 2013
Appl. No.: 12/501,883
Filed: Jul. 13, 2009

( * ) Notice: This patent is subject to a terminal disclaimer.

Related U.S. Application Data

(62) Division of application No. 11/975,511, filed on Oct. 19, 2007, now Pat. No. 7,662,980.

(60) Provisional application No. 60/853,341, filed on Oct. 20, 2006.

(51) Int. Cl.
*C07D 305/14* (2006.01)

(52) U.S. Cl.
USPC .......................................... 549/510; 549/511

(58) Field of Classification Search
None
See application file for complete search history.

(56) References Cited

To view the complete listing of prior art documents cited during the proceeding for Reexamination Control Number 90/012,941, please refer to the USPTO's public Patent Application Information Retrieval (PAIR) system under the Display References tab.

*Primary Examiner* — Alan Diamond

(57) ABSTRACT

New anhydrous crystalline form of docetaxel and process of making anhydrous docetaxel and docetaxel trihydrate are provided.

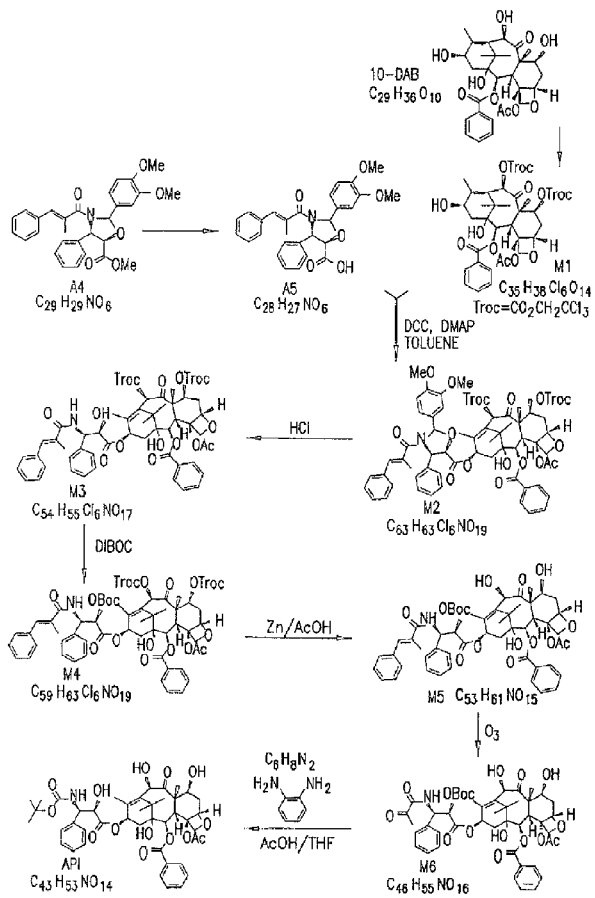

US 8,357,811 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-3 are cancelled.

Claims 5 and 6 are determined to be patentable as amended.

New claim 7 is added and determined to be patentable.

Claim 4 was not reexamined.

5. The crystalline anhydrous N-debenzoyl-N-tert-butoxycarbonyl-10-deacetyl taxol of claim [1] *7* further characterized by an infrared spectrum having bands at about 710, 1248, 1723, 2978, and 3430 ($cm^{-1}$).

6. The crystalline anhydrous N-debenzoyl-N-tert-butoxycarbonyl-10-deacetyl taxol of claim [1] *7* further characterized by an infrared spectrum as substantially depicted in FIG. 10.

*7. Crystalline anhydrous N-debenzoyl-N-tert-butoxycarbonyl-10-deacetyl taxol characterized by a powder x-ray diffraction pattern with peaks at 8.0, 11.3, 12.4, 13.8, 15.4, 16.8, 20.3, and 23.3±0.2 degrees two-theta, and the powder x-ray diffraction pattern is substantially depicted in FIG. 3.*

\* \* \* \* \*